United States Patent
Lee et al.

(10) Patent No.: US 9,427,476 B2
(45) Date of Patent: Aug. 30, 2016

(54) MULTIVALENT MENINGOCOCCAL CONJUGATES AND METHODS FOR PREPARING CONJUGATES

(71) Applicants: The United States of America, as represented by the Secretary, Department of Health and Human Services, Washington, DC (US); The United States of America, as Represented by the Secretary of the Army, Washington, DC (US)

(72) Inventors: Che-Hung Robert Lee, Silver Spring, MD (US); Valerian B. Pinto, Frederick, MD (US)

(73) Assignees: The United States of America, as represented by the Secretary, Department of Health and Human Services, Washington, DC (US); The United States of America, as Represented by the Secretary of the Army, Washington, DC (US)

( * ) Notice: Subject to any disclaimer, the term of this patent is extended or adjusted under 35 U.S.C. 154(b) by 0 days.

(21) Appl. No.: 14/402,988

(22) PCT Filed: May 23, 2013

(86) PCT No.: PCT/US2013/042428
§ 371 (c)(1),
(2) Date: Nov. 21, 2014

(87) PCT Pub. No.: WO2013/177397
PCT Pub. Date: Nov. 28, 2013

(65) Prior Publication Data
US 2015/0110829 A1   Apr. 23, 2015

Related U.S. Application Data

(60) Provisional application No. 61/651,382, filed on May 24, 2012.

(51) Int. Cl.
*A61K 39/095* (2006.01)
*A61K 47/48* (2006.01)
*A61K 39/00* (2006.01)

(52) U.S. Cl.
CPC ......... *A61K 47/4833* (2013.01); *A61K 39/095* (2013.01); *A61K 2039/572* (2013.01); *A61K 2039/70* (2013.01)

(58) Field of Classification Search
CPC .............. A61K 39/095; A61K 2039/55505; A61K 2039/55566; A61K 2039/572; A61K 2039/70; A61K 47/4833; C07K 14/22
See application file for complete search history.

(56) References Cited

U.S. PATENT DOCUMENTS

| | | | |
|---|---|---|---|
| 2007/0110762 | A1 | 5/2007 | Jessouroun et al. |
| 2007/0141084 | A1 | 6/2007 | Lee et al. |
| 2008/0025993 | A1 | 1/2008 | Biemans et al. |
| 2011/0020390 | A1 | 1/2011 | Pizza et al. |
| 2012/0064104 | A1 | 3/2012 | Costantino |

FOREIGN PATENT DOCUMENTS

| | | |
|---|---|---|
| WO | WO 2007/109129 | 9/2007 |
| WO | WO 2010/109324 | 9/2010 |
| WO | WO 2011/103588 | 8/2011 |
| WO | WO 2011/110634 | 9/2011 |

OTHER PUBLICATIONS

Beernink et al., "Meningococcal Factor H-Binding Protein Variants Expressed by Epidemic Capsular Group A, W-135, and X Strains from Africa," *J. Inf. Dis.* vol. 199, pp. 1360-1368, 2009.
Kohn et al., "The Use of Cyanogen Bromide and Other Novel Cyanylating Agents for the Activation of Polysaccharide Resins," *Applied Biochemistry and Biotechnology*, vol. 9, No. 3, pp. 285-305, 1984.
Lewis et al., "The Meningococcal Vaccine Candidate Neissertial Surface Protein A (NspA) Binds to Factor H and Enhances Meningococcal Resistance to Complement," *PLoS Pathogens* 6:e1001027, 2010 (20 pages).
Masignani et al., "Vaccination against *Neisseria meningitidis* Using Three Variants of the Lipoprotein GNA1870," *J. Exp. Med.*, vol. 197, No. 6, pp. 789-799, 2003.
Moe et al., "Sequential Immunization with Vesicles Prepared from Heterologous *Neisseria meningitides* Strains Elicits Broadly Protective Serum Antibodies to Group B Strains," *Infection and Immunity*, vol. 70, No. 11, pp. 6021-6031, 2002.
Seib et al., "Influence of serogroup B meningococcal vaccine antigens on growth and survival of the meningococcus *in vitro* and in *ex vivo* and *in vivo* models of infection," *Vaccine*, vol. 28, No. 12, pp. 2416-2427, 2010.
Weynants et al., "Genetically Modified L3,7 and L2 Lipooligosaccharides from *Neisseria meningitidis* Serogroup B Confer a Broad Cross-Bactericidal Response," *Inf. Immun.* vol. 77, No. 5, pp. 2084-2093, 2009.

*Primary Examiner* — Padma V Baskar
(74) *Attorney, Agent, or Firm* — Klarquist Sparkman, LLP

(57) ABSTRACT

Disclosed herein are meningococcal immunogenic conjugates which can elicit immune responses against meningococcal polysaccharides (PS) from groups A, C, W-135, and Y and group B factor H binding protein (fHbp). The disclosed conjugates also exhibit bactericidal activity against meningococcal A, C, W-135, Y, B, and X serogroups. Also disclosed are improved methods for preparing conjugates, such as immunogenic conjugates, including activation of a polysaccharide with a cyanylation agent at about 4° C.

6 Claims, 4 Drawing Sheets

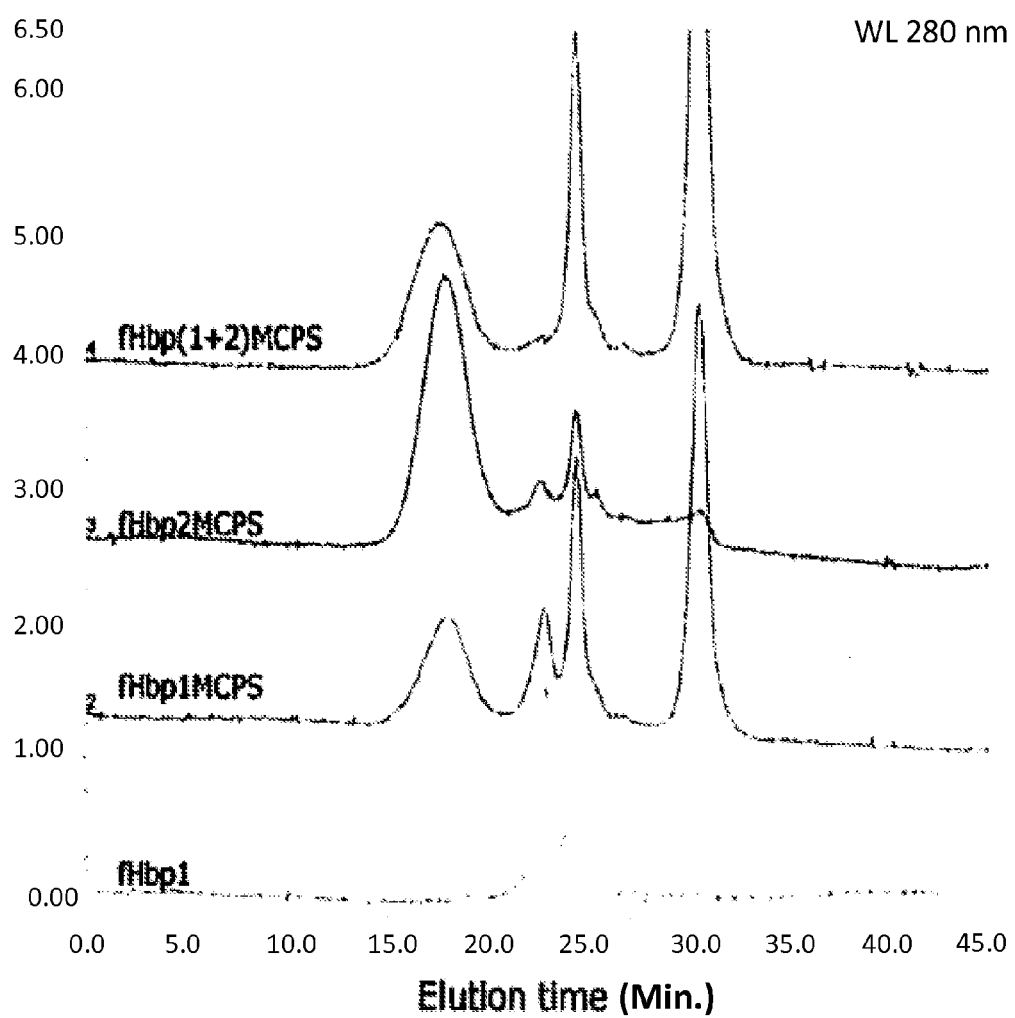

MULTIVALENT MENINGOCOCCAL CONJUGATES AND METHODS FOR PREPARING CONJUGATES

CROSS REFERENCE TO RELATED APPLICATIONS

This is the §371 U.S. National Stage of International Application No. PCT/US2013/042428, filed May 23, 2013, which was published in English under PCT Article 21(2), which in turn claims the benefit of U.S. Provisional Application No. 61/651,382, filed May 24, 2012, which is incorporated herein by reference in its entirety.

FIELD

This disclosure relates to conjugates, particularly immunogenic meningococcal conjugates, and methods of making such conjugates.

BACKGROUND

Among thirteen isolated meningococcal serogroups, A, B, C, W-135, and Y are the most prevalent. There are three FDA-approved capsular polysaccharide (PS)-based vaccines—Menomune® tetravalent PS vaccine (Sanofi Pasteur), and Menactra® (Sanofi Pasteur) and Menveo® (Novartis) tetravalent conjugate vaccines for protection against meningococcal disease caused by groups A, C, W-135, and Y *Neisseria meningitidis*. Group B capsular PS, a polysialic acid with an α2→8 glycosidic linkage, is similar to the PS structure expressed in certain human tissues (Finne et al., *Lancet* 2:355-357, 1983), thus making it a poor immunogen. Furthermore, if used as a vaccine, the possibility exists of it inducing an autoimmune response. Thus, a need remains to develop additional meningococcal vaccines, particularly for group B and group X meningococcal serogroups.

SUMMARY

Disclosed herein are immunogenic conjugates including at least one polysaccharide or protein conjugated to a *Neisseria* surface protein, for example group B factor H binding protein (fHbp) or *Neisseria* surface protein A (NspA). In some examples, the conjugates are meningococcal immunogenic conjugates which can elicit immune responses against meningococcal polysaccharides (PS) from groups A, C, W-135, and Y. In additional examples, the immunogenic conjugates can also elicit immune responses against fHbp or NspA. In further examples, the disclosed conjugates also exhibit bactericidal activity against meningococcal A, C, W-135, Y, B, and X serogroups. In some examples, the immunogenic conjugates are multivalent immunogenic conjugates.

Also disclosed are improved methods for preparing conjugates, including such immunogenic conjugates. In some embodiments, the methods include reacting at least one first moiety (such as a PS, protein, drug, or other compound) with a cyanylation agent at about 2° C. to about 6° C., resulting in a cyanate-activated first moiety and contacting the cyanate-activated first moiety with a second moiety (such as a PS, protein, drug, or other compound) having at least one amino group or at least one hydrazide group (such as a hydrazide-activated second moiety) at about 2° C. to about 6° C., resulting in a conjugate that includes at least one C—N bond formed between the at least one first moiety and the at least one second moiety.

In some non-limiting embodiments, the methods include reacting at least one polysaccharide with a cyanylation agent at about 2° C. to about 6° C., resulting in a cyanate-activated polysaccharide and contacting the cyanate-activated polysaccharide with at least one protein (such as fHbp or NspA), resulting in an immunogenic conjugate that includes at least one C—N bond formed between the at least one polysaccharide and the at least one protein. In some examples, the methods also include reacting the at least one protein with hydrazine, carbohydrazide, hydrazine chloride, a dihydrazide, or a mixture thereof at about 2° C. to about 6° C., producing a solution of at least one hydrazide-activated protein and contacting the at least one cyanate-activated polysaccharide with at least one protein at about 2° C. to about 6° C., such that the at least one cyanate-activated polysaccharide reacts with the at least one hydrazide-activated protein, resulting in an immunogenic conjugate that includes at least one C—N bond formed between the at least one polysaccharide and the at least one protein The foregoing and other features of the disclosure will become more apparent from the following detailed description, which proceeds with reference to the accompanying figures.

BRIEF DESCRIPTION OF THE DRAWINGS

FIG. 1A is a digital image of SDS-PAGE analysis: fHbp1 in lane 1; fHbp2 in lane 2; fHbp(1+2) in lane 3; and the molecular weight ladder in lane 4. FIG. 1B is a digital image of a Western blot analysis using monoclonal antibodies Jar 5 (specific to fHbp1) and Jar 11 (specific to fHbp 2). fHbp(1+2) in lanes 1 and 4 was developed with monoclonal antibodies Jar 5 and Jar 11, respectively; fHbp1 in lane 2 was developed with monoclonal antibody Jar 5; and fHbp2 in lane 3 was developed with monoclonal antibody Jar 11.

FIGS. 3A and 3B are a set of HPLC profiles of conjugate products. FIG. 3A is a set of HPLC profiles of fHbp1 and conjugate products of fHbp1MCPS, fHbp2MCPS, and fHbp(1+2)MCPS monitored at 280 nm. The protein signals move from low molecular weight elution time (about 23 minutes) to high molecular weight position (about 17.5 minutes) upon conjugation. FIG. 3B is a set of HPLC profiles of fHbp(1+2) and conjugate products of fHbp(1+2) and meningococcal serogroup A polysaccharide (MAPS), fHbp(1+2)MCPS, fHbp(1+2) and meningococcal serogroup W-135 polysaccharide (MWPS), and fHbp(1+2) and meningococcal serogroup Y polysaccharide (MYPS) monitored at 280 nm. The protein signals move from about 22.5 minutes to about 15.5-18.5 minutes upon conjugation.

SEQUENCE LISTING

Figure 1A:
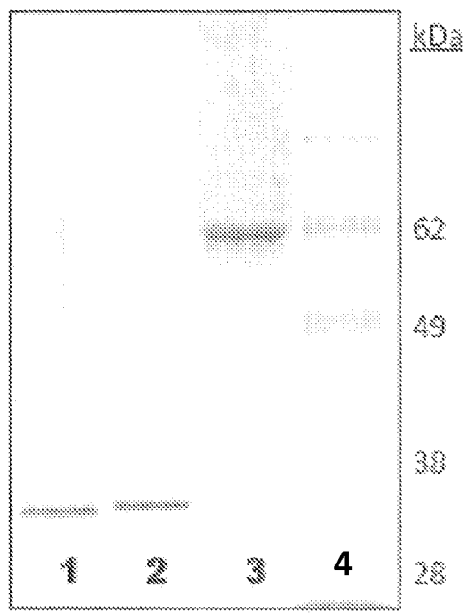
FIG. 1A-1B are a pair of digital images of purified recombinant meningococcal factor H binding protein variant 1 (fHbp1), variant 2 (fHbp2), and their fusion product (fHbp(1+2)).

Any nucleic acid and amino acid sequences listed herein or in the accompanying sequence listing are shown using standard letter abbreviations for nucleotide bases and amino acids, as defined in 37 C.F.R. §1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Nov. 20, 2014, and is 18,139 bytes, which is incorporated by reference herein.

SEQ ID NOs: 1 and 2 are exemplary NspA nucleic acid and amino acid sequences, respectively.

SEQ ID NOs: 3 and 4 are exemplary fHbp1 nucleic acid and amino acid sequences, respectively.

SEQ ID NOs: 5 and 6 are exemplary fHbp2 nucleic acid and amino acid sequences, respectively.

SEQ ID NOs: 7 and 8 are exemplary fHbp1-fHbp2 fusion nucleic acid and amino acid sequences, respectively.

SEQ ID NOs: 9 and 10 are the nucleic acid sequences of forward and reverse fHbp1 primers, respectively.

SEQ ID NOs: 11 and 12 are the nucleic acid sequences of forward and reverse fHbp2 primers, respectively.

SEQ ID NOs: 13 and 14 are the nucleic acid sequences of additional reverse fHbp1 primers.

SEQ ID NOs: 15 and 16 are the nucleic acid sequences of additional forward fHbp2 primers.

DETAILED DESCRIPTION

Kohn and Wilchek first introduced 1-cyano-4-dimethylaminopyridinium tetrafluoroborate (CDAP as a substitute for CNBr in the activation of the hydroxyl group on PS resins (*Appl. Biochem. Biotech.* 9:285-305, 1984). Designated protein was then mixed with and conjugated to the activated PS resins for affinity chromatography. This method was subsequently used to activate soluble PS to prepare PS-protein conjugates (e.g., Lees et al., *Vaccine* 26:190-198, 1996). This method required 2-2.5 minutes activation time for PS at pH 9 at room temperature in order to achieve optimal yield of conjugate product.

Disclosed herein are conjugation methods which avoid the inconvenient and less controllable procedure of 2-2.5 minutes PS activation time. It was found that PS can be activated by CDAP at about 4° C. for 1.5-3 hours and achieve better yield of conjugation with protein. Without being bound by theory, it may be that CDAP and the resulting cyanate groups have longer half-life at lower temperatures (e.g., 4° C.) than at room temperature. A similar phenomenon was observed for PS conjugating to hydrazide groups in hydrazide-activated protein at 4° C. Thus, the disclosed methods provide advantages for production of polysaccharide-protein conjugates, including improved control, convenience, and yield. These features may be particularly advantageous for large-scale production of conjugates, for example, for commercial vaccine production.

The disclosed improved conjugation methods are not limited to production of conjugates of PS and proteins. These improved methods can be utilized for conjugation of any cyanate-activated moiety with any moiety including an amino group or any hydrazide-activated moiety, providing improved convenience and increased yield of the resulting conjugate. For example, the disclosed methods can be used to produce chemical, biochemical, medical, pharmacological, diagnostic and/or therapeutic reagents.

I. Abbreviations

ADH adipic acid dihydrazide
APDO 1-amino-2,3-propanediol
CAPS 3-(cyclohexylamino)-1-propanesulfonicacid
CDAP 1-cyano-4-dimethylaminopyridinium tetrafluoroborate
CHES (2-(N-cyclohexylamino)ethane sulfonic acid
EDC 1-[3-(dimethylamino)propyl]-3-ethylcarbodiimide hydrochloride
fHbp factor H binding protein
fHbp1 factor H binding protein 1 (subfamily B)
fHbp2 factor H binding protein 2 (subfamily A)
HEPES N-(2-Hydroxyethyl) piperazine-N'-(2-ethanesulfonic acid)
MAPS meningococcal serogroup A polysaccharide
MCPS meningococcal serogroup C polysaccharide
MWPS meningococcal serogroup W-135 polysaccharide
MYPS meningococcal serogroup Y polysaccharide
NspA *Neisseria* surface protein A
PS polysaccharide
TT tetanus toxoid II. Terms Unless otherwise explained, all technical and scientific terms used herein have the same meaning as commonly understood by one of ordinary skill in the art to which this disclosure belongs. The singular terms "a," "an," and "the" include plural referents unless the context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety for all purposes. All GenBank Accession Nos. mentioned herein are incorporated by reference in their entirety as of May 24, 2012. In case of conflict, the present specification, including explanations of terms, will control. In addition, the materials, methods, and examples are illustrative only and not intended to be limiting.

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adjuvant: A substance or vehicle that non-specifically enhances the immune response to an antigen. Adjuvants can include a suspension of minerals (such as alum, aluminum hydroxide, or phosphate) on which antigen is adsorbed or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218, 371; 6,239,116; 6,339,068; 6,406,705; and 6,429,199). Adjuvants also include biological molecules, such as costimulatory molecules. Exemplary biological adjuvants include IL-2, RANTES, GM-CSF, TNF-α, IFN-γ, G-CSF, LFA-3, CD72, B7-1, B7-2, OX-40L and 41 BBL.

Antigen: A compound, composition, or substance that may be specifically bound by the products of specific humoral or cellular immunity, such as an antibody molecule or T-cell receptor. Antigens can be any type of biologic molecule including, for example, simple intermediary metabolites, sugars (e.g., oligosaccharides), lipids, and hormones as well as macromolecules such as complex carbohydrates (e.g., polysaccharides), phospholipids, nucleic acids and proteins. Categories of antigens include, but are not limited to, viral antigens, bacterial antigens, fungal antigens, protozoa and other parasitic antigens, tumor antigens, antigens involved in autoimmune disease, allergy and graft rejection, toxins, and other miscellaneous antigens.

Carrier: An immunogenic molecule to which a hapten or an antigen (such as a polysaccharide), can be bound or conjugated. When bound or conjugated to a carrier, the molecule may become more immunogenic. Carriers are chosen to increase the immunogenicity of the bound or conjugated molecule and/or to elicit antibodies against the carrier which are diagnostically, analytically, and/or therapeutically beneficial. Covalent linking of a molecule to a carrier can confer enhanced immunogenicity and T-cell dependence (Pozsgay et al., *PNAS* 96:5194-97, 1999; Lee et al., *J. Immunol.* 116:1711-18, 1976; Dintzis et al., *PNAS* 73:3671-75, 1976). Useful carriers include polymeric carriers, which can be natural (for example, proteins from bacteria or viruses), semi-synthetic, or synthetic materials containing one or more functional groups to which a reactant moiety can be attached.

Examples of bacterial products for use as carriers include bacterial toxins, such as *B. anthracis* protective antigen (including fragments that contain at least one antigenic epitope and analogs or derivatives capable of eliciting an immune response), lethal factor and lethal toxin, and other bacterial toxins and toxoids, such as tetanus toxin/toxoid, diphtheria toxin/toxoid, *P. aeruginosa* exotoxin/toxoid, pertussis toxin/toxoid, and *C. perfringens* exotoxin/toxoid. As disclosed herein, meningococcal factor H binding proteins or NspA proteins are also useful carrier proteins. Viral proteins, such as hepatitis B surface antigen and core antigen can also be used as carriers.

Conjugate (conjugating): Coupling a first unit to a second unit. This includes, but is not limited to, covalently bonding one molecule to another molecule (for example, directly or via a linker molecule), noncovalently bonding one molecule to another (e.g. electrostatically bonding) (see, for example, U.S. Pat. No. 6,921,496, which discloses methods for electrostatic conjugation), non-covalently bonding one molecule to another molecule by hydrogen bonding, non-covalently bonding one molecule to another molecule by van der Waals forces, and any and all combinations of such couplings. In one embodiment, conjugating includes covalent bond linkage of a polysaccharide to a protein. The covalent bond linkage can be direct or indirect, e.g., linked though a spacer molecule.

Covalent bond: An interatomic bond between two atoms, characterized by the sharing of one or more pairs of electrons by the atoms. The terms "covalently bound" or "covalently linked" refer to making two separate molecules into one contiguous molecule.

Effective amount: A quantity of a specified agent sufficient to achieve a desired effect in a subject being treated with that agent. For example, this may be the amount of an immunogenic conjugate (such as a meningococcal PS-fHbp conjugate) useful in increasing resistance to, preventing, ameliorating, and/or treating infection and disease caused by a bacterial infection in a subject. A therapeutically effective amount of an agent may include an amount sufficient to increase resistance to, prevent, ameliorate, and/or treat infection and disease caused by infection in a subject without causing a substantial cytotoxic effect in the subject. The effective amount or therapeutically effective amount of an agent useful for increasing resistance to, preventing, ameliorating, and/or treating infection and disease caused by infection in a subject will be dependent on the subject being treated, the severity of the affliction, and the manner of administration of the composition.

Factor H binding protein (fHbp): A meningococcal surface protein, also known as GNA1870 or LP2086 (Masignani et al., *J. Exp. Med.* 197:789-799, 2003; Fletcher et al., *Inf. Immun.* 72:2088-2100, 2004). fHbp binds to factor H, which is a cofactor in the cleavage of C3b to iC3b, prevents association of factor B with C3b slowing formation of the alternative pathway C3 convertase, and irreversibly dissociates the C3 convertase once it is formed. There are two subfamilies of fHbp, subfamily A (also referred to as fHbp2) and subfamily B (also referred to as fHbp1). The fHbp proteins exhibit substantial sequence variation among *N. meningitidis* strains, but all bind to factor H.

fHbp nucleic acid and protein sequences are publicly available. Exemplary fHbp nucleic acid sequences include GenBank Accession Nos. NC_003112 (1975218-1976180), AY330353, AY330354, AY330363, AY330361, AY330367, AY330370, AY330375, AY330398, AY330399, AY330400, AY330401, AY330406, AY330407, AY330408, AY330409, AY330411, JN580522, and the associated amino acid sequences, all of which are incorporated herein by reference as present in GenBank on May 24, 2012. One of skill in the art can identify additional fHbp nucleic acid and protein sequences.

Immune response: A response of a cell of the immune system, such as a B-cell, T-cell, macrophage or polymorphonucleocyte, to a stimulus. An immune response can include any cell of the body involved in a host defense response for example, an epithelial cell that secretes interferon or a cytokine. An immune response includes, but is not limited to, an innate immune response or inflammation.

Immunogen: A compound, composition, or substance which is capable, under appropriate conditions, of stimulating the production of antibodies or a T-cell response in a subject, including compositions that are injected or absorbed into a subject.

Immunogenic conjugate or composition: A composition useful for stimulating or eliciting a specific immune response (or immunogenic response) in a subject. In some embodiments, the immunogenic response is protective or provides protective immunity, in that it enables the subject to better resist infection or disease progression from the organism against which the immunogenic composition is directed. One specific example of a type of immunogenic composition is a vaccine.

Immunogenic-distinct polysaccharide: A polysaccharide that elicits an immune response that differs from the immune response elicited by another type of polysaccharide. Immunogenic-distinct polysaccharides may be two or more polysaccharides from different encapsulated bacteria. For example, a pneumococcal polysaccharide is an immunogenic-distinct polysaccharide compared to a meningococcal polysaccharide. Immunogenic-distinct polysaccharides also are inclusive of two or more polysaccharides from different serogroups or serotypes. For example, a meningococcal polysaccharide of serogroup A is an immunogenic-distinct polysaccharide compared to a meningococcal polysaccharide of serogroup C.

Inhibiting or treating a disease: "Inhibiting" a disease refers to inhibiting the full development of a disease or condition, for example, in a subject who is at risk for a disease such as meningococcal meningitis. Inhibition of a disease can span the spectrum from partial inhibition to substantially complete inhibition (prevention) of the disease. In some examples, the term "inhibiting" refers to reducing or delaying the onset or progression of a disease. "Treatment" refers to a therapeutic intervention that ameliorates a sign or symptom of a disease or pathological condition after it has begun to develop. As used herein, the term "ameliorating," with reference to a disease, pathological condition or symptom, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease.

Multivalent immunogenic conjugate or multivalent conjugate vaccine: A molecule or conjugate including more than one antigenic epitope. One type of a multivalent immunogenic conjugate includes a mixture of different molecules, each molecule comprising different immunogenic-distinct polysaccharides wherein each different immunogenic-distinct polysaccharide is conjugated to a separate protein carrier (which may be the same or different protein carriers). Another type of a multivalent immunogenic conjugate is a molecule in which a plurality of immunogenic-distinct polysaccharides are conjugated to a single protein molecule or single protein construct (which protein construct itself includes more than one different protein). A further type of multivalent immunogenic conjugate includes a mixture of the conjugates of the first type and the conjugates of the second type. An example of the first type of multivalent immunogenic conjugate may be depicted as a mixture of the different structures represented by:

$P^1$-$PS^1$; $P^1$-$PS^2$; and $P^1$-$PS^3$ wherein $P^1$ is a carrier protein; and $PS^1$, $PS^2$, and $PS^3$ are each immunogenic-distinct polysaccharides.

An example of the second type of multivalent immunogenic conjugate may be depicted as a structure represented by:

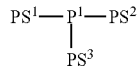

wherein $P^1$ is a carrier protein; $PS^1$, $PS^2$, and $PS^3$ are each immunogenic-distinct polysaccharides that are covalently attached to $P^1$.

The protein and polysaccharide in the above formulae can be singular or plural structural units, and there is at least one bond formed between the protein and the polysaccharide.

*Neisseria meningitidis*: A bacterium which causes meningococcal meningitis in humans. There are at least thirteen serogroups of *N. meningitis*, including groups A, B, C, W-135, X, Y, D, 29E, H, I, K, L, and Z, which are classified based on the composition of their polysaccharide capsule. Of these, A, B, C, W-135, X, and Y account for the majority of meningococcal disease. Symptoms of meningococcal meningitis include stiff neck, high fever, light sensitivity, headaches, and vomiting. Even with early diagnosis and antibiotic treatment, 5-10% of infected individuals die. Meningococcal meningitis may also result in brain damage or hearing loss in 10-20% of those who survive the disease. Meningococcal disease may also progress to meningococcal septicemia, characterized by hemorrhagic rash and rapid circulatory collapse.

*N. meningitidis* bacteria are spread through contact with respiratory or throat secretions of carriers (such as through coughing, sneezing, kissing, sharing food or utensils, and living in close proximity). Up to 10-20% of the population may carry the bacteria in the nasopharynx without symptoms at any given time and the carriage rate may be even higher during an epidemic.

Neisserial surface protein A (NspA): A meningococcal surface protein capable of binding to factor H (Lewis et al., *PloS Pathogens* 6:e1001027).

NspA nucleic acid and protein sequences are publicly available. Exemplary NspA nucleic acid sequences include GenBank Accession Nos. NC_003112.2 (690298 . . . 690822, complement), NC_013016.1 (590409 . . . 590933, complement), NC_010120.1 (632166 . . . 632690, complement), and NC_008767.1 (635025 . . . 635549, complement) and their associated amino acid sequences, all of which are incorporated by reference as present in GenBank on May 24, 2012. One of skill in the art can identify additional NspA sequences.

Pharmaceutically acceptable carrier: The pharmaceutically acceptable carriers (vehicles) useful in this disclosure are conventional. *Remington: The Science and Practice of Pharmacy*, The University of the Sciences in Philadelphia, Editor, Lippincott, Williams, & Wilkins, Philadelphia, Pa., $21^{st}$ Edition (2005), describes compositions and formulations suitable for pharmaceutical delivery of one or more therapeutic compounds or molecules, such as one or more disclosed immunogenic conjugates, and additional pharmaceutical agents.

Subject: Living multi-cellular vertebrate organisms, a category that includes both human and non-human mammals. Subjects include veterinary subjects, including livestock such as cows and sheep, rodents (such as mice and rats), and non-human primates.

III. Immunogenic Conjugates

Disclosed herein are novel immunogenic conjugates which include a polysaccharide (such as one or more bacterial polysaccharides) or a protein (such as a bacterial surface protein or an immunogenic portion thereof) conjugated to a carrier protein, for example, a *Neisseria* surface protein, such as meningococcal fHbp or NspA. The disclosed conjugates are immunogenic in a subject (as demonstrated in the Examples, below).

In particular non-limiting embodiments, the disclosed immunogenic conjugates include one or more (such as 1, 2, 3, 4, or more) immunogenic-distinct polysaccharides conjugated to fHbp or NspA. In particular examples, the immunogenic conjugates include one or more meningococcal polysaccharides (such as one or more meningococcal serogroups A, C, W-135, Y, or X polysaccharides) conjugated to fHbp or NspA. In other examples, the immunogenic conjugates include one or more pneumococcal, group B streptococcal, *Haemophilus influenzae* type b, or *Salmonella typhi* polysaccharides conjugated to fHbp or NspA.

In other embodiments, the disclosed immunogenic conjugates include one or more (such as 1, 2, 3, 4, or more) proteins or an immunogenic portion thereof conjugated to a carrier protein, such as fHbp or NspA. In some examples, the immunogenic conjugates include one or more bacterial surface proteins conjugated to fHbp. In other examples, the immunogenic conjugates include one or more bacterial surface proteins conjugated to NspA.

In some embodiments, the immunogenic conjugates are multivalent immunogenic conjugates, such as a conjugate including more than one antigenic epitope. In some examples, a multivalent immunogenic conjugate includes a mixture of different molecules, each molecule including different immunogenic-distinct polysaccharides wherein each different immunogenic-distinct polysaccharide is conjugated to a separate protein carrier (each of which may be the same or different protein carriers). In one non-limiting example, such a multivalent immunogenic conjugate may be depicted as a mixture of the different structures represented by:

$P^1$-$PS^1$; $P^1$-$PS^2$; and $P^1$-$PS^3$ or
$P^2$-$PS^1$; $P^2$-$PS^2$; and $P^2$-$PS^3$, wherein $P^1$ and $P^2$ are carrier proteins (for example fHbp and NspA); and $PS^1$, $PS^2$, and $PS^3$ are each immunogenic-distinct polysaccharides.

In other examples, a multivalent immunogenic conjugate includes molecules in which a plurality of immunogenic-distinct polysaccharides are conjugated to a single protein molecule or single protein construct (which protein construct itself includes more than one different protein). A non-limiting example of such a multivalent conjugate may be depicted as a structure represented by:

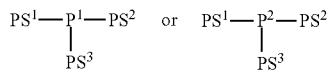

wherein $P^1$ and $P^2$ are carrier proteins (such as fHbp and NspA); $PS^1$, $PS^2$, and $PS^3$ are each immunogenic-distinct polysaccharides that are covalently attached to $P^1$ or $P^2$.

In yet another example, a multivalent immunogenic conjugate includes a mixture of one or more of the conjugates described above. In one example, a multivalent immunogenic conjugate includes a mixture of conjugates of MAPS-fHbp, MCPS-fHbp, MWPS-fHbp, and MYPS-fHbp. In another example, a multivalent immunogenic conjugate can also include a mixture of one or more immunogenic conjugates of a polysaccharide conjugated to fHbp and one or more immunogenic conjugates of a polysaccharide conjugated to NspA.

A. Polysaccharides

The term "polysaccharide" as used herein, is a broad term and is used in its ordinary sense, including, without limitation, saccharides comprising a plurality of repeating units, including, but not limited to polysaccharides having 50 or more repeat units, and oligosaccharides having 50 or less repeating units. Typically, polysaccharides have from about 50, 55, 60, 65, 70, 75, 80, 85, 90, or 95 repeating units to about 2,000 or more repeating units, and such as from about 100, 150, 200, 250, 300, 350, 400, 500, 600, 700, 800, 900 or 1000 repeating units to about, 1100, 1200, 1300, 1400, 1500, 1600, 1700, 1800, or 1900 repeating units. Oligosac-charides typically have from about 6, 7, 8, 9, or 10 repeating units to about 15, 20, 25, 30, or 35 to about 40 or 45 repeating units.

In some examples, polysaccharides for use in the disclosed conjugates and methods include polysaccharides and oligosaccharides from encapsulated bacteria. The polysaccharides and oligosaccharides can be from any source, for example, they can be derived from naturally-occurring bacteria, genetically engineered bacteria, or can be produced synthetically. The polysaccharides and oligosaccharides can be subjected to one or more processing steps prior to activation, for example, purification, functionalization, depolymerization using mild oxidative conditions, deacetylation, and the like. Post processing steps can also be employed, if desired. Any suitable method known in the art for synthesizing, preparing, and/or purifying suitable polysaccharides and oligosaccharides can be employed.

Polysaccharides and oligosaccharides for use in the disclosed conjugates and methods include pneumococcal polysaccharides of, for example, serogroups 1, 2, 3, 4, 5, 6B, 7F, 8, 9N, 9V, 10A, 11A, 12F, 14, 15B, 17F, 18C, 19A, 19F, 20, 22F, 23F and 33F; meningococcal polysaccharides of serotypes A, B, C, W-135, and Y, *Haemophilus influenzae* type b polysaccharide polyribosylribitol phosphate, group B streptococcal polysaccharides of serotypes III and V, and *Salmonella typhi* Vi polysaccharide. Other polysaccharides of pneumococcal and group B streptococcal serotypes, and meningococcal serogroups are also suitable for use herein, as are other T-independent polysaccharide and oligosaccharide antigens, for example, polysaccharides or oligosaccharides derived from group A *streptococcus, Staphylococci, Enterococci, Klebsiella pneumoniae, E. coli, Pseudomonas aeruginosa*, and *Bacillus anthracis*. While bacterial polysaccharides and oligosaccharides are particularly suitable, gram-negative bacterial lipopolysaccharides and lipooligosaccharides and their polysaccharide and oligosaccharide derivatives, and viral polysaccharides and oligosaccharides can also be employed. In one example, detoxified mutant meningococcal lipooligosaccharides can be used in the disclosed conjugates (see, e.g., Weynants et al., *Inf. Immun.* 77:2084-2093, 2009).

Polysaccharides with side chain phosphorus and/or backbone phosphorus are suitable for use in the disclosed conjugates and methods. The conjugation reactions (such as those described in Section IV, below) are particularly well suited for use with polysaccharides having phosphorus in the backbone, although they are not limited to such polysaccharides.

B. Carrier Proteins

In some embodiments, the disclosed immunogenic conjugates include a polysaccharide or at least a portion of (such as an immunogenic portion of) one or more (such as 1, 2, 3, 4, or more) proteins (such as one or more bacterial surface proteins) conjugated to a carrier protein. In some examples, the carrier protein is a *Neisseria* surface protein. In particular embodiments, the carrier protein is fHbp. In some examples, the immunogenic conjugate includes a meningococcal polysaccharide or protein conjugated to fHbp. In other embodiments, the carrier protein is NspA. In some examples, the immunogenic conjugate includes a meningococcal polysaccharide or protein conjugated to NspA. In other examples, the immunogenic conjugate includes meningococcal outer membrane vesicles or meningococcal outer membrane protein mixture conjugated to fHbp or NspA.

Nucleic acid and amino acid sequences of NspA are publicly available. In some examples, an NspA protein is encoded by a nucleic acid sequence at least 70% (such as at least 75%, 80%, 85%, 90%, 95%, 96%, 97%, 98%, 99%, or even 100%) identical to the nucleic acid sequence set forth as SEQ ID NO: 1. In some examples, an NspA protein is at least 70% (such as at least 75%, 80%, 85%, 90%, 95%, 96%, 97%, 98%, 99%, or even 100%) identical to the amino acid sequence set forth as SEQ ID NO: 2.

Factor H binding protein (fHbp) is a meningococcal surface protein, also known as GNA1870 or LP2086 (Masignani et al., *J. Exp. Med.* 197:789-799, 2003; Fletcher et al., *Inf. Immun.* 72:2088-2100, 2004). fHbp binds to factor H, which is a cofactor in the cleavage of C3b to iC3b, prevents association of factor B with C3b slowing formation of the alternative pathway C3 convertase, and irreversibly dissociates the C3 convertase once it is formed. There are two subfamilies of fHbp, subfamily A (also referred to as fHbp2) and subfamily B (also referred to as fHbp1).

Nucleic acid and amino acid sequences of fHbp1 are publicly available. In some examples, an fHbp1 protein is encoded by a nucleic acid sequence at least 70% (such as at least 75%, 80%, 85%, 90%, 95%, 96%, 97%, 98%, 99%, or even 100%) identical to the nucleic acid sequence set forth as SEQ ID NO: 3. In some examples, an fHbp1 protein is at least 70% (such as at least 75%, 80%, 85%, 90%, 95%, 96%, 97%, 98%, 99%, or even 100%) identical to the amino acid sequence set forth as SEQ ID NO: 4.

Nucleic acid and amino acid sequences of fHbp2 are publicly available. In some examples, an fHbp2 protein is encoded by a nucleic acid sequence at least 70% (such as at least 75%, 80%, 85%, 90%, 95%, 96%, 97%, 98%, 99%, or even 100%) identical to the nucleic acid sequence set forth as SEQ ID NO: 5. In some examples, an fHbp2 protein is at least 70% (such as at least 75%, 80%, 85%, 90%, 95%, 96%, 97%, 98%, 99%, or even 100%) identical to the amino acid sequence set forth as SEQ ID NO: 6.

In some examples, the immunogenic conjugates include a fusion protein including at least a portion of each of fHbp1 and fHbp2. In one example, an fHbp1-fHbp2 fusion protein is encoded by a nucleic acid encoding fHbp1 (or a portion thereof), which is directly or indirectly (for example via a linker) linked to a nucleic acid encoding fHbp2 (or a portion thereof). In some examples, an fHbp1-fHbp2 fusion protein is encoded by a nucleic acid sequence at least 70% (such as at least 75%, 80%, 85%, 90%, 95%, 96%, 97%, 98%, 99%, or even 100%) identical to the nucleic acid sequence set forth as SEQ ID NO: 7. In some examples, an fHbp-1fHbp2 fusion protein is at least 70% (such as at least 75%, 80%, 85%, 90%, 95%, 96%, 97%, 98%, 99%, or even 100%) identical to the amino acid sequence set forth as SEQ ID NO: 8.

IV. Methods of Preparing Immunogenic Conjugates

The disclosed immunogenic conjugates can be prepared by methods including reductive amination conjugation or cyanylation conjugation. In some examples, the methods for preparing the immunogenic conjugates are standard methods known to one of skill in the art. In other examples, the methods are improved methods that provide, for example, increased convenience, improved ability to perform large scale reactions, and increased yield over standard methods. The improved methods can be utilized to prepare a conjugate between any cyanate-activated moiety (such as a PS, protein, drug, or other compound) and any moiety (such as a PS, protein, drug, or other compound) with at least one amino group or any hydrazide-activated moiety (such as a PS, protein, drug, or other compound). One of skill in the art will recognize that the improved methods are not limited to production of immunogenic conjugates, such as those disclosed herein.

A. Reductive Amination Conjugation

In some embodiments, methods of preparing the disclosed immunogenic conjugates include reductive amination reaction to conjugate a polysaccharide containing aldehyde groups to a protein (such as hydrazide modified protein). In some examples, the methods include reacting at least one polysaccharide with an oxidizing agent, resulting in at least one aldehyde-activated polysaccharide; reacting at least one protein with hydrazine, carbohydrazide, hydrazine chloride, a dihydrazide, or a mixture thereof, resulting in at least one hydrazide-activated protein; and contacting the at least one aldehyde-activated polysaccharide with the at least one hydrazide-activated protein, resulting in a conjugate with one or more C=N double bonds between at least one polysaccharide and at least one protein. In some examples, the methods further include reducing substantially all of the C=N double bonds of the conjugate to C—N bonds (for example with sodium borohydride). Exemplary methods include those in International Patent Publication Nos. WO 2005/014037, WO 2005/037320, and WO 2007/109129, all of which are incorporated herein by reference in their entirety. In some examples, the disclosed methods include conjugating at least one aldehyde-activated meningococcal PS (such as MAPS, MCPS, MWPS, MYPS, or a combination of two or more thereof) to a hydrazide-activated fHbp.

Any suitable functionalization reaction can be employed to activate the polysaccharide or oligosaccharide with aldehyde groups. Certain polysaccharides and oligosaccharides possess terminal aldehyde groups that can participate in the conjugation reaction. If the polysaccharide or oligosaccharide is activated with aldehyde groups, a preferred reaction involves reaction with an oxidizing agent, such as $NaIO_4$. Oxidizing agents have the potential for fragmenting the polysaccharide or oligosaccharide. Undesirable fragmentation can be avoided or controlled through selection of the particular oxidizing agent and the concentration of the oxidizing agent employed. Ketone groups are also capable of reacting with hydrazide, so activation of the polysaccharide or oligosaccharide with ketone groups can be employed in certain embodiments. In some examples, polysaccharide is reacted with sodium periodate at about 2-6° C. (for example, about 2° C., about 2.5° C., about 3° C., about 3.5° C., about 4° C., about 4.5° C., about 5° C., about 5.5° C., or about 6° C.) for 6-24 hours (for example about 6, about 7, about 8, about 9, about 10, about 11, about 12, about 13, about 14, about 15, about 16, about 17, about 18, about 19, about 20, about 21, about 22, about 23, or about 24 hours) or overnight. The activated polysaccharide can be purified, for example by diafiltration against water.

In some examples, a strongly buffered (e.g., at pH of from about 6.5 to about 8, with a high buffer concentration of from about 100 mM to about 200 mM) activated polysaccharide solution is employed in the conjugation reaction in the form of a strongly buffered solution. Any suitable buffer can be employed, such as a buffer such as N-(2-Hydroxyethyl) piperazine-N'-(2-ethanesulfonic acid) (HEPES) or phosphate buffered saline. In other examples, the activated polysaccharide is buffer exchanged with 10 mM HEPES, pH 7.5.

In some examples, the methods include introducing at least one hydrazide group onto the protein (for example, a carrier protein, such as a fHbp or NspA) by reacting the protein with excess hydrazine, carbohydrazide, hydrazine chloride, or a dihydrazide (for example, succinyl dihydrazide or adipic acid dihydrazide (ADH)) catalyzed by a carbodiimide (such as 1-[3-(dimethylamino)propyl]-3-ethylcarbodiimide hydrochloride (EDC), although any water-soluble carbodiimide can be used). In some examples, the protein is reacted with hydrazine or ADH in the presence of EDC at about pH 5.5-6.5 (such as pH about 5.5, about 5.6, about 5.7, about 5.8, about 5.9, about 6.0, about 6.1, about 6.2, about 6.3, about 6.4, or about 6.5).

In some examples, the hydrazide-activated protein is maintained soluble at a pH of from about 10 to about 11.5, such as from about 10.1, 10.2, 10.3, or 10.4 to about 10.6, 10.7, 10.8, 10.9, 11.0, 11.1, 11.2, 11.3, or 11.4, for example about 10.5, with a buffer at a concentration of from about 3 or less to about 10 mM or more, such as from about 4 or 5 mM to about 6, 7, 8, or 9; mM, before conjugation. Suitable buffers include but are not limited to $Na_2CO_3$, 3-(cyclohexylamino)-1-propanesulfonic acid (CAPS), and (2-(N-cyclohexylamino)ethane sulfonic acid (CHES). In one example, the hydrazide-activated protein is buffer-exchanged to a solution of about pH 10.5 (such as 30 mM NaCl and 3 mM $Na_2CO_3$, pH 10.5). In other examples, the hydrazide-activated protein is maintained soluble at neutral or approximately neutral pH (e.g., pH of about 7 to about 7.5) by activating the protein in the presence of at least one amino acid (such as lysine, arginine, histidine, glycine, serine, threonine, glutamic acid, cysteine, or a mixture of two or more thereof) (see, e.g., WO 07/109129, incorporated herein by reference). Amino acids may be included in the activation reaction at a concentration of about 1-500 mM, about 20-300 mM, or about 36-144 mM.

The hydrazide-based conjugation reaction can be carried to completion within one to three days at reactant concentrations of from about 1 to about 40 mg/mL, or about 1 to about 50 mg/mL, at PS/protein weight ratios of from about 1:5 to about 5:1, such as from about 1:2 to about 2:1, for example, about 1:1, although in certain embodiments higher or lower ratios can be utilized. In some examples, the conjugation reaction is conducted at temperatures of from about 4° C. to about 40° C., for example from about 4, 10, 15, or 20° C. to about 25, 30, or 35° C., and at a pH of from about 6 to about 8.5, such as from about 6.1, 6.2, 6.3, 6.4, or 6.5 to about 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, or 8.4, with optimal conditions varying according to the polysaccharide.

In conventional reductive amination, the reaction between aldehyde and amino groups is reversible and unfavorable, such that sodium cyanoborohydride is needed to facilitate the conjugation by converting the C=N double bond to a C—N single bond to render the entire reductive amination event irreversible. In contrast, the reductive amination conjugation reaction of the disclosed methods proceeds without the aid of sodium cyanoborohydride because of the high efficiency of the hydrazide-aldehyde reaction. At the end of the reductive amination conjugation reaction, sodium borohydride or another suitable reductant is employed to reduce the C=N double bond to a C—N single bond, as well as to reduce any residual aldehyde groups to alcohol groups. The reductive amination conjugation reaction of these methods avoids contamination of the resulting conjugate with cyanide, a by-product of sodium cyanoborohydride.

To reduce precipitation of activated protein during the conjugation reaction, the activated protein is provided in the form of a weakly buffered solution with a low buffer concentration of from about 3 mM to about 10 mM, which is added to a strongly buffered (at pH of from about 6.5 to about 7.5, with a high buffer concentration of from about 100 mM to about 200 mM) activated polysaccharide solution. In particular examples, the pH of the activated protein solution is buffered to from about pH 10 to about pH 11.5, for example, about pH 10.5. The activated polysaccharide solution is strongly buffered to from about pH 6 to about pH8, such as from about pH 6.5 to about pH 7.5. The hydrazide-aldehyde reductive amination reaction proceeds at a fast rate, and the precipitating effect of a pH lower than 10.5 (for example, a pH as low as from about 8.5 to about 9.5) on activated protein is overcome by the molecular properties of the reacting activated polysaccharide.

In another embodiment, the disclosed methods include reacting at least one aldehyde-activated protein with at least one hydrazide-activated polysaccharide to produce an immunogenic conjugate. Any suitable functionalization reaction can be employed to activate the protein with aldehyde groups. In one example, the protein is reacted with 1-amino-2,3-propanediol (APDO) in the presence of EDC. Amino sugars such as glucosamine, galactosamine, and the like can be used in place of APDO. In one example, the methods include reacting at least one protein with APDO in the presence of EDC at a pH of from about 6 to about 7, whereby a solution of a APDO-modified protein is obtained; buffer exchanging the solution of the APDO-modified protein to a pH of from about 10.0 to about 11.0; reacting the APDO-modified protein with an oxidizing agent, whereby a solution of an aldehyde-activated protein is obtained; buffer exchanging the solution of the aldehyde-activated protein to a pH of from about 10.0 to about 11.0; reacting a hydrazide-activated polysaccharide with the aldehyde-activated protein at a pH of from about 6 to about 8, whereby a conjugate comprising one or more C=N double bonds is obtained; and reducing substantially all of the C=N double bonds of the conjugate to C—N single bonds. In some examples, the hydrazide-activated polysaccharide is obtained by reacting a polysaccharide with an oxidizing agent (for example, $NaIO_4$) in a solution, producing an aldehyde-activated polysaccharide; reacting the aldehyde-activated polysaccharide with ADH to produce an intermediate including one or more C=N double bonds; and reducing substantially all of the C=N double bonds of the intermediate to C—N single bonds (for example with $NaBH_4$), producing a hydrazide-activated polysaccharide.

B. Cyanylation Conjugation

In other embodiments, methods of preparing conjugates (such as the disclosed immunogenic conjugates) include a cyanylation conjugation reaction to conjugate a moiety containing at least one cyanate group to a moiety including at least one amino group or to at least one hydrazide-activated moiety. In some examples, the methods include conjugating a polysaccharide containing cyanate groups to a protein (such as a native protein or a hydrazide modified protein). In some embodiments, the improved cyanylation conjugation methods disclosed herein include reacting at least one first moiety (such as a PS, protein, drug, or other compound) with a cyanylation agent at about 2° C. to about 6° C., resulting in a cyanate-activated first moiety and contacting the cyanate-activated first moiety with a second moiety (such as a PS, protein, drug, or other compound) having at least one amino group or at least one hydrazide group (such as a hydrazide-activated second moiety) at about 2° C. to about 6° C., resulting in a conjugate that includes at least one C—N bond formed between the at least one first moiety and the at least one second moiety. The resulting conjugates are useful for a variety of purposes, including as immunogenic, diagnostic, and/or therapeutic compounds or reagents. One of skill in the art can select appropriate moieties for conjugation by the cyanylation conjugation methods provided herein, and the methods are not limited to production of the specific examples provided herein.

In some examples, the disclosed methods include reacting at least one polysaccharide with a cyanylation agent, resulting in at least one cyanate-activated polysaccharide. In some embodiments, the at least one cyanate-activated polysaccharide is reacted with at least one protein, resulting in a conjugate that includes at least one C—N bond formed between at least one polysaccharide and at least one protein. In other embodiments, the at least one cyanate-activated polysaccharide is reacted with a hydrazide-activated protein. Thus, in some examples, the methods also include reacting at least one protein with hydrazine, carbohydrazide, hydrazine chloride, a dihydrazide or a mixture thereof, resulting in at least one hydrazide-activated protein. Exemplary methods include those in International Patent Publication Nos. WO 2005/014037, WO 2005/037320, and WO 2007/109129, all of which are incorporated herein by reference in their entirety. In some examples, the disclosed methods include conjugating at least one cyanate-activated meningococcal PS (such as MAPS, MCPS, MWPS, MYPS, or a combination of two or more thereof) to a fHbp protein (such as a native fHbp or a hydrazide-activated fHbp). In other examples, the disclosed methods include conjugating at least one cyanate-activated meningococcal PS (such as MAPS, MCPS, MWPS, MYPS, or a combination of two or more thereof) to a NspA protein.

Any suitable functionalization reaction can be employed to activate the polysaccharide or oligosaccharide with cyanate groups. In one non-limiting example, the polysaccharide or oligosaccharide is reacted with 1-cyano-4-dimethylammoniumpyridinium tetrafluoroborate (CDAP) in the presence of triethylamine. Additional cyanylation agents include cyanogen bromide, p-nitrophenyl cyanate (pNPC), 1-cyano-4-pyrrolidiniopyridinium tetrafluoroborate (CPIP), and N-cyano-N,N,N-triethylammonium tetrafluoroborate (CTEA).

In some examples, at least one polysaccharide is reacted with a cyanylation agent (for example CDAP) at about 20° C.-25° C. (such as about 20° C., about 21° C., about 22° C., about 23° C., about 24° C., or about 25° C.) in the presence of triethylamine for about 1-5 minutes (such as about 1, about 1.5, about 2, about 2.5, about 3, about 3.5, about 4, about 4.5, or about 5 minutes). In other examples, at least one polysaccharide is reacted with a cyanylation agent (such as CDAP) at about 2° C.-6° C. (such as about 2° C., about 2.5° C., about 3° C., about 3.5° C., about 4° C., about 4.5° C., about 5° C., about 5.5° C., or about 6° C., for example about 4° C.) in the presence of triethylamine for about 1-3 hours (for example about 1, about 1.5, about 2, about 2.5, or about 3 hours).

Activation of polysaccharide with a cyanylation agent (such as CDAP) at about 4° C. for longer times is more convenient and easier to control than the conventional activation for short periods of time at room temperature. In particular, a longer reaction time makes the method more suitable for large scale preparation of immunogenic conjugates, for example for commercial vaccine production. In addition, the modified activation conditions provide increased yield following conjugation to a protein (such as a hydrazide-activated protein) than are achieved with the standard (room temperature) activation conditions. In some examples, the yield of the immunogenic conjugate is about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 3-fold, about 4-fold, about 5-fold more, or higher when the activation reaction is carried out at 4° C. than when it is carried out at room temperature. In some examples, the amount of unconjugated protein in the reaction is reduced from about 30% when the reaction is carried out at room temperature, to less than about 5% when the reaction is carried out a 4° C., corresponding to about a 40% increase in conjugation yield In some examples, the methods also include introducing at least one hydrazide group onto the protein (for example, a carrier protein, such as a fHbp) by reacting the protein with excess hydrazine, carbohydrazide, hydrazine chloride, or a dihydrazide (for example, succinyl dihydrazide or adipic acid dihydrazide (ADH)) catalyzed by a carbodiimide (such as 1-[3-(dimethylamino)propyl]-3-ethylcarbodiimide hydrochloride (EDC), although any water-soluble carbodiimide can be used). In some examples, the protein is reacted with hydrazine or ADH in the presence of EDC at about pH 5.5-6.5 (such as pH about 5.5, about 5.6, about 5.7, about 5.8, about 5.9, about 6.0, about 6.1, about 6.2, about 6.3, about 6.4, or about 6.5).

In some examples, the hydrazide-activated protein is maintained soluble at a pH of from about 10 to about 11.5, such as from about 10.1, 10.2, 10.3, or 10.4 to about 10.6, 10.7, 10.8, 10.9, 11.0, 11.1, 11.2, 11.3, or 11.4, for example about 10.5, with a buffer at a concentration of from about 3 or less to about 10 mM or more, such as from about 4 or 5 mM to about 6, 7, 8, or 9; mM, before conjugation. Suitable buffers include but are not limited to $Na_2CO_3$, 3-(cyclohexylamino)-1-propanesulfonicacid (CAPS), and (2-(N-cyclohexylamino)ethane sulfonic acid (CHES). In one example, the hydrazide-activated protein is buffer-exchanged to a solution of about pH 10.5 (such as 30 mM NaCl and 3 mM $Na_2CO_3$, pH 10.5). In other examples, the hydrazide-activated protein is maintained soluble at neutral or approximately neutral pH (e.g., pH of about 7 to about 7.5) by activating the protein in the presence of at least one amino acid (such as lysine, arginine, histidine, glycine, serine, threonine, glutamic acid, cysteine, or a mixture of two or more thereof) (see, e.g., WO 07/109129). Amino acids may be included in the activation reaction at a concentration of about 1-500 mM, about 20-300 mM, or about 36-144 mM.

The cyanylation conjugation reaction is efficient and reversible, favoring the product formation. In certain embodiments, blocking agents are employed to remove residual cyanate groups. However, addition of a blocking agent to the reaction mixture drives the conjugation reaction backward and reduces the conjugation yield by 5-12%. While in certain embodiments it can be desirable to employ blocking agents (for example, ADH, hydrazine, glycine, or ethanolamine) to quench the leftover residual cyanate groups, it is generally preferred to avoid their use so as to avoid reduction in conjugate yield. To remove residual cyanate groups in the conjugation product without using a blocking agent, the conjugation time can be prolonged. In some examples, conjugation is conducted at a temperature of from about 0° C. to about 6° C. (for example, about 2° C., about 2.5° C., about 3° C., about 3.5° C., about 4° C., about 4.5° C., about 5° C., about 5.5° C., or about 6° C.) for about 36 to about 48 hours, for example at about 4° C. for about 36 hours, followed by about an additional 18 to 24 hours at a temperature of from about 20° C. to about 25° C., for example at about 18 hours at about 20 to 24° C., such that the residual cyanate groups react with water and decompose. Longer or shorter conjugation times and/or higher or lower conjugation temperatures can be employed, and different sequences of steps at various times and temperatures can be conducted, as desired. It is desirable, however, to conduct the conjugation reaction, at least initially, at low temperatures, for example from about 0° C. to about 6° C., such as about 2° C. to about 6° C. (for example, about 2° C., about 2.5° C., about 3° C., about 3.5° C., about 4° C., about 4.5° C., about 5° C., about 5.5° C., or about 6° C.), so as to reduce the degree of precipitation of the conjugate. In particular examples, the reaction is carried out at about 4° C.

C. Preparation of Multivalent Immunogenic Conjugates

In some embodiments, the disclosed methods utilize a plurality of immunogenic-distinct polysaccharides and/or a plurality of proteins to produce a multivalent immunogenic conjugate. For example, a mixture of two or more (such as 2, 3, 4, 5, or more) immunogenic-distinct polysaccharides (e.g., a plurality of immunogenic-distinct polysaccharides) is conjugated to at least one protein (such as fHbp or NspA) using the methods described above. In some examples the plurality of immunogenic distinct polysaccharides includes two or more meningococcal polysaccharides (for example, two or more of meningococcal polysaccharides selected from serotypes A, B, C, W-135, and Y). In one particular example, the plurality of immunogenic distinct polysaccharides includes meningococcal serogroup A polysaccharide (MAPS), meningococcal serogroup C polysaccharide (MCPS), meningococcal serogroup W-135 polysaccharide (MWPS), and meningococcal serogroup Y polysaccharide (MYPS). In other examples, the plurality of immunogenic-distinct polysaccharides includes polysaccharides from two or more different bacteria (such as two or more of meningococcal polysaccharides, pneumococcal polysaccharides, *Haemophilus influenzae* type b polysaccharide, Vi polysaccharide of *Salmonella typhi*, and group B *Streptococcus* polysaccharides). In one particular example, the plurality of immunogenic-distinct polysaccharides includes at least one meningococcal polysaccharide, at least one pneumococcal polysaccharide, and at least one *Haemophilus influenzae* type b polysaccharide.

In some examples, a mixture of more than one polysaccharide (such as a plurality of immunogenic-distinct polysaccharides) can be simultaneously activated by reaction with a single activating agent (or a mixture of activating agents) in single batch step. In one example, a mixture of MAPS, MCPS, MWPS, and MYPS can be reacted with an aldehyde-functionalizing agent in a single batch reaction. In another example, a mixture of MAPS, MCPS, MWPS, and MYPS can be reacted with cyanate-functionalizing agent in a single batch reaction. In additional examples, a mixture of at least one meningococcal polysaccharide (such as at least one of meningococcal polysaccharides of serotypes A, B, C, W-135, and Y), at least one pneumococcal polysaccharide (such as at least one of pneumococcal polysaccharides of serogroups 1, 2, 3, 4, 5, 6B, 7F, 8, 9N, 9V, 10A, 11A, 12F, 14, 15B, 17F, 18C, 19A, 19F, 20, 22F, 23F and 33F), and at least one *H. influenzae* type b polysaccharide can be activated with an aldehyde-functionalizing agent of a cyanate-functionalizing agent. The mixture of activated polysaccharides is then conjugated to at least one protein (such as fHbp or NspA) in a single process.

In yet another example, each individual polysaccharide can be activated by reaction with an activating agent in a separate process. The separately activated polysaccharides can then be mixed together prior to the conjugation step so the activated polysaccharides can be simultaneously conjugated in a single process.

In still further examples, multivalent immunogenic conjugates are prepared by mixing individual immunogenic conjugates. For example, a multivalent immunogenic conjugate can be prepared by mixing conjugates of MAPS-fHbp, MCPS-fHbp, MWPS-fHbp, and MYPS-fHbp. A multivalent immunogenic conjugate can also be prepared by mixing one or more immunogenic conjugates of a polysaccharide conjugated to fHbp and one or more immunogenic conjugates of a polysaccharide conjugated to NspA.

The activation and conjugation reactions can be carried out according to the methods described above.

V. Methods of Eliciting an Immune Response or Inhibiting or Treating Infection

The conjugates disclosed herein and/or prepared according to the methods disclosed herein are administered to a subject in an effective dose (for example, a therapeutically effective dose) in a suitable form to elicit an immune response in the subject. In some embodiments, the disclosed immunogenic conjugates are capable of treating, inhibiting, or in some examples, even preventing infection or disease (for example *Neisseria meningitidis* infection) in a subject. A subject, as used herein, refers to animals, such as mammals. For example, mammals include humans, primates, dogs, cats, sheep, cattle, goats, pigs, horses, mice, rats, rabbits, guinea pigs, and the like. The terms subject, patient, and host are used interchangeably. The particular dosage effective to elicit an immune response or to treat, inhibit, or ameliorate an infection depends upon the age, weight and medical condition of the subject to be treated, as well as on the method of administration. Immunization protocols for use with the disclosed conjugates provide compositions and methods for preventing or treating a disease, disorder and/or infection in a subject are known to one of skill ordinary in the art. Suitable doses and immunization protocols can be readily determined by those of ordinary skill in the art.

Pharmaceutical compositions comprising the disclosed conjugates can offer various advantages over conventional vaccines, including enhanced immunogenicity of weakly immunogenic antigens, potential reduction in the amount of antigen used, less frequent booster immunizations, improved efficacy, preferential stimulation of immunity, or potential targeting of immune responses. The disclosed immunogenic conjugates, conjugates made by the disclosed methods, and/or pharmaceutical compositions including the conjugates can be administered to a subject by a variety of routes, as discussed below, including but not limited to parenteral, intradermal, transmembranal, transdermal (including topical), intramuscular, intraperitoneal, intravenous, intra-arterial, intralesional, subcutaneous, oral, and intranasal (e.g., inhalation) routes of administration. Immunogenic conjugates can be administered by bolus injection or by continuous infusion, as well as by localized administration, for example at a site of disease or injury. The conjugate can be optionally administered in a pharmaceutically or physiologically acceptable carrier (vehicle).

One or more of the disclosed conjugates (such as 2, 3, 4, 5, 6, or more) can be formulated with adjuvants, diluents, excipients, carriers, and other pharmaceutically acceptable substances. The term "pharmaceutically acceptable" is used to refer to a non-toxic material that is compatible with a biological system such as a cell, cell culture, tissue, or organism. In some examples, the disclosed compositions are sterile and contain either a therapeutically or prophylactically effective amount of the conjugate in a unit of weight or volume suitable for administration to a subject. The pharmaceutically acceptable carriers (vehicles) useful in this disclosure are conventional. *Remington: The Science and Practice of Pharmacy*, The University of the Sciences in Philadelphia, Editor, Lippincott, Williams, & Wilkins, Philadelphia, Pa., 21$^{st}$ Edition (2005), describes compositions and formulations suitable for pharmaceutical delivery of one or more therapeutic compounds or molecules. The characteristics of the carrier depend on the route of administration. Physiologically and pharmaceutically acceptable carriers include diluents, fillers, salts, buffers, stabilizers, solubilizers, and other materials which are well known in the art.

Formulation of the immunogenic conjugates into pharmaceutical compositions can be accomplished using methods known in the art. In some examples, the compositions can also contain one or more adjuvants. Suitable adjuvants include, for example, aluminum adjuvants (such as aluminum hydroxide or aluminum phosphate), Freund's Adjuvant, BAY, 3(N,N,-dimethylaminoethane)-carbamyl cholesterol (DC-Chol), poly[di(sodium carboxylatephoneoxy) phosphazene] (PCPP), monophosphoryl lipid A, CpG, QS-21, cholera toxin, and formyl methionyl peptide. See, e.g., *Vaccine Design, the Subunit and Adjuvant Approach*, 1995 (M. F. Powell and M. J. Newman, eds., Plenum Press, N.Y.).

The dosage of immunogenic conjugate(s) to be administered to a subject and the regime of administration can be determined in accordance with standard techniques well known to those of ordinary skill in the pharmaceutical and veterinary arts, taking into consideration such factors as the intended use, particular antigen, the adjuvant (if present), the age, sex, weight, species, general condition, prior illness and/or treatments of the subject, and the route of administration. Preliminary doses can be determined according to animal tests, and the scaling of dosages for human administration is performed according to art-accepted practices such as standard dosing trials. For example, the therapeutically effective dose can be estimated initially from serum antibody level testing. The dosage depends on the specific activity of the conjugate and can be readily determined by routine experimentation.

In practicing immunization protocols for inhibition, treatment, and/or prevention of specified diseases, a therapeutically effective amount of conjugate is administered to a subject. In some examples, a therapeutically effective amount is the total amount of therapeutic agent (e.g., conjugate) or other active component that is sufficient to show a meaningful benefit to the subject, such as immune response, treatment, healing, inhibition, prevention, or amelioration of the relevant medical condition (disease, infection, or the like), or an increase in rate of treatment, healing, prevention or amelioration of such conditions. An effective amount can include the amount of an individual therapeutic agent (such as an individual immunogenic conjugate disclosed herein), a combination of therapeutic agents (such as two or more of the disclosed immunogenic conjugates), or a combination of one or more of the disclosed immunogenic conjugates and other agents. A combination can be administered to a subject simultaneously, substantially simultaneously, or serially. In particular examples, a subject is administered an amount of therapeutic agent or composition in an amount and for a time to treat, inhibit, or even prevent an infection, such as an infection with *Neisseria meningitidis*.

Generally, the amount of conjugate that is an effective amount or a therapeutically effective amount is from about 1 µg/kg or less to about 100 µg/kg or more, such as from about 2, 3, 4, 5, 6, 7, 8, 9, 10, 15, 20, 25, 30, 35, 40, 45 or 50 µg/kg to about 55, 60, 65, 70, 75, 80, 85, 90, or 95 µg/kg body weight. An effective amount can be less if the post-infection time elapsed is less, since there is less time for the pathogen to proliferate. An effective amount can also depend on the bacterial load at the time of diagnosis. Multiple injections administered over a period of days can be considered for therapeutic usage.

The disclosed immunogenic conjugates can be administered as a single dose or in a series including one or more boosters. For example, a subject can receive a single dose (for example, early in life), then be administered a booster dose up to 1 month, 2 months, 3 months, 6 months, 1 year, 2 years, 3 years, 4 years, 5 years, 6 years, 7 years, 8 years, 9 years, 10 years, or more later. More than one booster dose can be administered if necessary, as determined by one of ordinary skill in the art. The booster dose generates antibodies from primed B-cells, for example, an anamnestic response. In some examples, the immunogenic conjugate elicits a high primary functional antibody response in infants or children, and is capable of eliciting an anamnestic response following a booster administration, demonstrating that the protective immune response elicited by the conjugate vaccine is long-lived.

The disclosed immunogenic conjugates can be formulated into liquid preparations for example, for oral, nasal, anal, rectal, buccal, vaginal, peroral, intragastric, mucosal, perlingual, alveolar, gingival, olfactory, or respiratory mucosa administration. Suitable forms for such administration include suspensions, syrups, and elixirs. The disclosed immunogenic conjugates can also be formulated for parenteral, subcutaneous, intradermal, intramuscular, intraperitoneal, or intravenous administration, injectable administration, sustained release from implants, or administration by eye drops. Suitable forms for such administration include sterile suspensions and emulsions. Such formulations can be in admixture with a suitable carrier, diluent, or excipient such as sterile water, physiological saline, glucose, and the like. The immunogenic conjugates can also be lyophilized. The immunogenic conjugates or formulations thereof can contain auxiliary substances such as wetting or emulsifying agents, pH buffering agents, gelling or viscosity enhancing additives, preservatives, flavoring agents, colors, and the like, depending upon the route of administration and the preparation desired. Such preparations can include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. The presence of such additional components can influence the physical state, solubility, stability, rate of in vivo release, and rate of in vivo clearance, and are thus chosen according to the intended application, such that the characteristics of the carrier are tailored to the selected route of administration.

The immunogenic conjugates may be provided as liquid suspensions or as freeze-dried products. Suitable liquid preparations include, for example, isotonic aqueous solutions, suspensions, emulsions, or viscous compositions that are buffered to a selected pH. Transdermal preparations include lotions, gels, sprays, ointments or other suitable techniques. If nasal or respiratory (mucosal) administration is desired (e.g., aerosol inhalation or insufflation), compositions can be in a form and dispensed by a squeeze spray dispenser, pump dispenser or aerosol dispenser. Aerosols are usually under pressure by means of a hydrocarbon. Pump dispensers can dispense a metered dose or a dose having a particular particle size, as discussed below.

When in the form of solutions, suspensions, or gels, formulations of the conjugate can typically contain a major amount of water (for example, purified water) in addition to the active ingredient. Minor amounts of other ingredients such as pH adjusters, emulsifiers, dispersing agents, buffering agents, preservatives, wetting agents, gelling agents, colors, and the like can also be present.

In specific examples, the compositions are isotonic with the blood or other body fluid of the subject. The isotonicity of the compositions can be attained using sodium tartrate, propylene glycol, or other inorganic or organic solutes. Sodium chloride is particularly preferred. Buffering agents can be employed, such as acetic acid and salts, citric acid and salts, boric acid and salts, and phosphoric acid and salts. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like.

Viscosity of the compositions can be maintained at the selected level using a pharmaceutically acceptable thickening agent. One suitable thickening agent is methylcellulose, because it is readily and economically available and is easy to work with. Other suitable thickening agents include, for example, xanthan gum, carboxymethyl cellulose, hydroxypropyl cellulose, carbomer, and the like. The concentration of the thickener can depend upon the agent selected and is used in an amount that can achieve the selected viscosity. Viscous compositions are normally prepared from solutions by the addition of such thickening agents.

A pharmaceutically acceptable preservative can be employed to increase the shelf life of the compositions. Benzyl alcohol can be suitable, although a variety of preservatives including, for example, parabens, thimerosal, chlorobutanol, or benzalkonium chloride can also be employed. A suitable concentration of the preservative can be from 0.02% to 2% based on the total weight although there can be appreciable variation depending upon the agent selected.

Pulmonary delivery of the conjugate can also be employed. The conjugate is delivered to the lungs of a mammal while inhaling and traverses across the lung epithelial lining to the blood stream. A wide range of mechanical devices designed for pulmonary delivery of therapeutic products can be employed, including but not limited to nebulizers, metered dose inhalers, and powder inhalers, all of which are familiar to those of ordinary skill in the art. These devices employ formulations suitable for the dispensing of the conjugate. Typically, each formulation is specific to the type of device employed and can involve the use of an appropriate propellant material, in addition to diluents, adjuvants, and/or carriers useful in therapy.

The conjugate is advantageously prepared for pulmonary delivery in particulate form with an average particle size of from 0.1 µm or less to 10 µm or more, more such as from about 0.2, 0.3, 0.4, 0.5, 0.6, 0.7, 0.8, or 0.9 µm to about 1.0, 1.5, 2.0, 2.5, 3.0, 3.5, 4.0, 4.5, 5.0, 5.5, 6.0, 6.5, 7.0, 7.5, 8.0, 8.5, 9.0, or 9.5 µm for pulmonary delivery. Pharmaceutically acceptable carriers for pulmonary delivery of the conjugates include carbohydrates such as trehalose, mannitol, xylitol, sucrose, lactose, and sorbitol. Other ingredients for use in pulmonary formulations can include dipalmitoylphosphatidylcholine (DPPC), dioleoyl phosphatidylethanolamine (DOPE), distearoyl phosphatidylcholine (DSPC), and dioleoyl phosphatidylcholine (DOPC). Natural or synthetic surfactants can be used, including polyethylene glycol and dextrans, such as cyclodextran. Bile salts and other related enhancers, as well as cellulose and cellulose derivatives, and amino acids can also be used. Liposomes, microcapsules, microspheres, inclusion complexes, and other types of carriers can also be employed.

Formulations suitable for use with a nebulizer, either jet or ultrasonic, typically comprise the conjugate dissolved or suspended in water at a concentration of about 0.01 mg or less to 100 mg or more of conjugate per mL of solution, such as from about 0.1, 1, 2, 3, 4, 5, 6, 7, 8, 9, or 10 mg to about 15, 20, 25, 30, 35, 40, 45, 50, 55, 60, 65, 70, 75, 80, 85, or 90 mg of conjugate per mL of solution. The formulation can also include a buffer and a simple sugar (for example, for protein stabilization and regulation of osmotic pressure). The nebulizer formulation can also contain a surfactant, to reduce or prevent surface induced aggregation of the conjugate caused by atomization of the solution in forming the aerosol.

Formulations for use with a metered-dose inhaler device generally comprise a finely divided powder containing the inventive compound suspended in a propellant with the aid of a surfactant. The propellant can include conventional propellants, such as a chlorofluorocarbon, a hydrochlorofluorocarbon, hydrofluorocarbons, and hydrocarbons, such as trichlorofluoromethane, dichlorodifluoroethane, dichlorotetrafluoroethanol, and 1,1,1,2-tetrafluoroethane, and combinations thereof. Suitable surfactants include sorbitan trioleate, soya lecithin, and oleic acid.

Formulations for dispensing from a powder inhaler device typically comprise a finely divided dry powder containing the conjugate, optionally including a bulking agent, such as lactose, sorbitol, sucrose, mannitol, trehalose, or xylitol in an amount that facilitates dispersal of the powder from the device, typically from about 1 wt. % or less to 99 wt. % or more of the formulation, such as from about 5, 10, 15, 20, 25, 30, 35, 40, 45, or 50 wt. % to about 55, 60, 65, 70, 75, 80, 85, or 90 wt. % of the formulation.

When the conjugate is administered by intravenous, cutaneous, subcutaneous, or other injection, the composition can be in the form of a pyrogen-free, parenterally acceptable aqueous solution. The preparation of parenterally acceptable solutions with suitable pH, isotonicity, stability, and the like, is within the ordinary skill in the art. In one example, a pharmaceutical composition for injection contains an isotonic vehicle such as Sodium Chloride Injection, Ringer's Injection, Dextrose Injection, Dextrose and Sodium Chloride Injection, Lactated Ringer's Injection, or other vehicles as are known in the art. The pharmaceutical compositions can also contain stabilizers, preservatives, buffers, antioxidants, or other additives known to those of ordinary skill in the art.

The duration of the injection can vary depending upon various factors, and can comprise a single injection administered over the course of a few seconds or less, to 1, 2, 3, 4, 5, 6, 7, 8, 9, 10, 11, 12, 13, 14, 15, 16, 17, 18, 19, 20, 21, 22, 23, or 24 hours or more of continuous intravenous administration.

The conjugate can be administered topically, systematically, or locally, via a liquid or gel, or as an implant or device.

The disclosed conjugates or the disclosed conjugation methods can be useful in preparing vaccines for the treatment, inhibition, or prevention of a variety of bacterial infections, including but not limited to infections by *Neisseria meningitidis, Neisseria gonorrhoeae, Streptococcus pneumoniae, Streptococcus pyogenes* (Group A *Streptococcus*), *Streptococcus agalaciae* (Group B *Streptococcus*), *Streptococcus* (*viridans* group), *Streptococcus faecalis*, Streptococcus bovis, Streptococcus (anaerobic sps.), Streptococcus pneumoniae, Haemophilus influenzae, and Salmonella typhi.

The conjugates can be administered in combination with various vaccines either currently being used or in development, whether intended for human or non-human subjects. Examples of vaccines for human subjects and directed to infectious diseases include combined diphtheria and tetanus toxoids vaccine; pertussis whole cell vaccine; inactivated influenza vaccine; 23-valent pneumococcal vaccine; live measles vaccine; live mumps vaccine; live rubella vaccine; Bacille Calmette-Guerin I (BCG) tuberculosis vaccine; hepatitis A vaccine; hepatitis B vaccine; hepatitis C vaccine; rabies vaccine (e.g., human diploid cell vaccine); inactivated polio vaccine; meningococcal polysaccharide vaccine (e.g., Menomune®, Sanofi Pasteur); quadrivalent meningococcal conjugate vaccine (e.g., Menactra® (Sanofi Pasteur) or Menveo® (Novartis)); yellow fever live virus vaccine; typhoid killed whole cell vaccine; cholera vaccine; Japanese B encephalitis killed virus vaccine; adenovirus vaccine; cytomegalovirus vaccine; rotavirus vaccine; varicella vaccine; anthrax vaccine; small pox vaccine; and other commercially available and experimental vaccines.

The conjugates can be provided to an administering physician or other health care professional in the form of a kit. The kit is a package which houses a container which contains the immunogenic conjugate and instructions for administering the composition to a subject. The kit can optionally also contain one or more other therapeutic agents. The kit can optionally contain one or more diagnostic tools and instructions for use. For example, a composition containing two or more of the disclosed immunogenic conjugates or other vaccines can be included, or separate pharmaceutical compositions containing different conjugates, vaccines, or therapeutic agents. The kit can also contain separate doses of the immunogenic conjugate for serial or sequential administration. The kit can contain suitable delivery devices, e.g., syringes, inhalation devices, and the like, along with instructions for administrating the therapeutic agents. The kit can optionally contain instructions for storage, reconstitution (if applicable), and administration of any or all therapeutic agents included. The kits can include a plurality of containers reflecting the number of administrations to be given to a subject. If the kit contains a first and second container, then a plurality of these can be present.

The disclosure is illustrated by the following non-limiting Examples.

Example 1

Preparation of Conjugates

Methods

MAPS was produced by SynCo BioPartners, Amsterdam, The Netherlands. MCPS was from FioCruz, BioMaguinhus, Brazil. MWPS and MYPS were from Chiron (Emoryville, Calif.). Tetanus toxoid (TT) was obtained from Wyeth Vaccines and Serum Institute of India. 1-cyano-4-dimethylaminopyridinium tetrafluoroborate (CDAP) was purchased from Sigma-Aldrich (St. Louis, Mo.).

The gene of fHbp1 was amplified by PCR using genomic N. meningitidis H44/76 genomic DNA as a template and forward primer AAGCTTCCTCGAGTGAGCAGTG-GAGGGGGTGGTGTCGCC (SEQ ID NO: 9) and reverse primer GGCGGGGAATTCACTTATTGCTTGGCG-GCAAGGCCGAT (SEQ ID NO: 10). The gene of fHbp2 was amplified by PCR using genomic N. meningitidis 7608 genomic DNA as a template and forward primer AAGCTTCCTCGAGTGAGCAGTGGAGGCGGCGGTGTCGCC (SEQ ID NO: 11) and reverse primer GGCGGGGAAT-TCACTTACTACTGTTTGCCGGCGATGCC (SEQ ID NO: 12). The PCR products were cloned in the XhoI-EcoRI site of pT7-MAT-Tag-Flag-1 vector (Sigma-Aldrich) which were then used to transform E. coli cells BL21(DE3). The transformed cells were grown in LB broth, induced with 1 mM IPTG, the cells were lysed, and the His-tagged proteins purified on Ni columns.

For the fHbp1/fHbp2 fusion protein (fHbp1+2), first the gene of fHbp1 was amplified by PCR using genomic N. meningitidis H44/76 genomic DNA as a template and the forward primer used for fHbp1 (SEQ ID NO: 9) and the reverse primer CGATCCGCCACCGCCAGAGCCACCTC-CGCCTGAACCGCCTCCACCTTGCTTGGCAAGG CCGAT (SEQ ID NO: 13). PCR product was reamplified using the same forward primer and the reverse primer GCCGCCTCCTCTAGAACCGCCACCGCCAGAGC-CACC (SEQ ID NO: 14). The gene of fHbp2 was amplified by PCR using genomic N. meningitidis 7608 genomic DNA as a template and the forward primer GGTGGAGGCGGT-TCAGGCGGAGGTGGCTCTGGCGGTGGCG-GATCGGGAGGCGGCGGT GTCGCC (SEQ ID NO: 15) and the reverse primer used for fHbp2 (SEQ ID NO: 12). The PCR product was reamplified using the forward primer GGTGGCGGTTCTAGAGGAGGCGGCGGTGTCGCC (SEQ ID NO: 16) and the same reverse primer. The fHbp1 PCR product was digested with XhoI and XbaI, while the fHbp2 PCR product was digested with XbaI and EcoRI. The digested products were cloned into the XhoI-EcoRI site of pT7-MATTag-Flag-1 vector (Sigma-Aldrich) which was then used to transform E. coli cells BL21(DE3). The transformed cells were grown in LB broth, induced with 1 mM IPTG, the cells were lysed and the His-tagged proteins purified on Ni columns.

The purified proteins were analyzed on 10% SDS-PAGE gels and Western blots using the Jar 5 and Jar 11 monoclonal antibodies.

Conjugation of polysaccharide to fHbp was carried out using CDAP conjugation method of Lees et al (Vaccine 26:190-198, 1996) with modification which involved carrying out the entire activation and conjugation reactions at 4° C. First, 10 μL PS (10 mg/mL; Mn A, C, W135 or Y) was mixed with 1 μL CDAP (100 mg/mL in acetonitrile), and then 1 μL triethylamine (TEA, 0.2 M) was added to the reaction mixture. After 1.5-2 hours incubation at 4° C., 4 μL of 0.1 M phosphate buffer, pH 5.5 was added to the reaction mixture followed by addition of 0.1 mg fHbp or hydrazide-modified TT prepared according to Lee et al. (Vaccine 27:726-732, 2009). The conjugation reaction proceeded overnight in a cold room with mixing by a rotary mixer. After dialysis against 10 mM HEPES, pH 7.2, 50 mM NaCl (4×1000 mL) at 4° C., the conjugation product was adjusted to [PS]=0.2 mg/mL with dialysis buffer and stored in refrigerator.

Samples of proteins, polysaccharides, and conjugate products (25 μL, 0.1 mg/mL) were applied to a Waters Ultrahydrogel™ 2000 column with 0.9% NaCl, 10 mM Tris (pH 7.2), 1 mM EDTA, at 0.5 mL/minute in a Dionex HPLC system using Chromelean® software with a UV detector at 280 nm for monitoring protein signal, and a refractive index detector for detecting protein, polysaccharide and conjugate.

Results

Figure 1B:
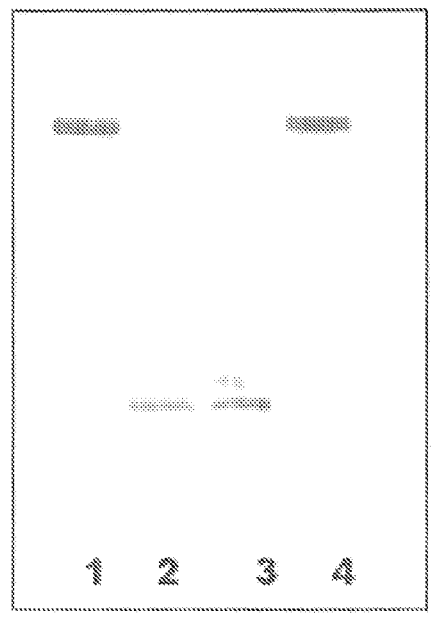
Figure 2:
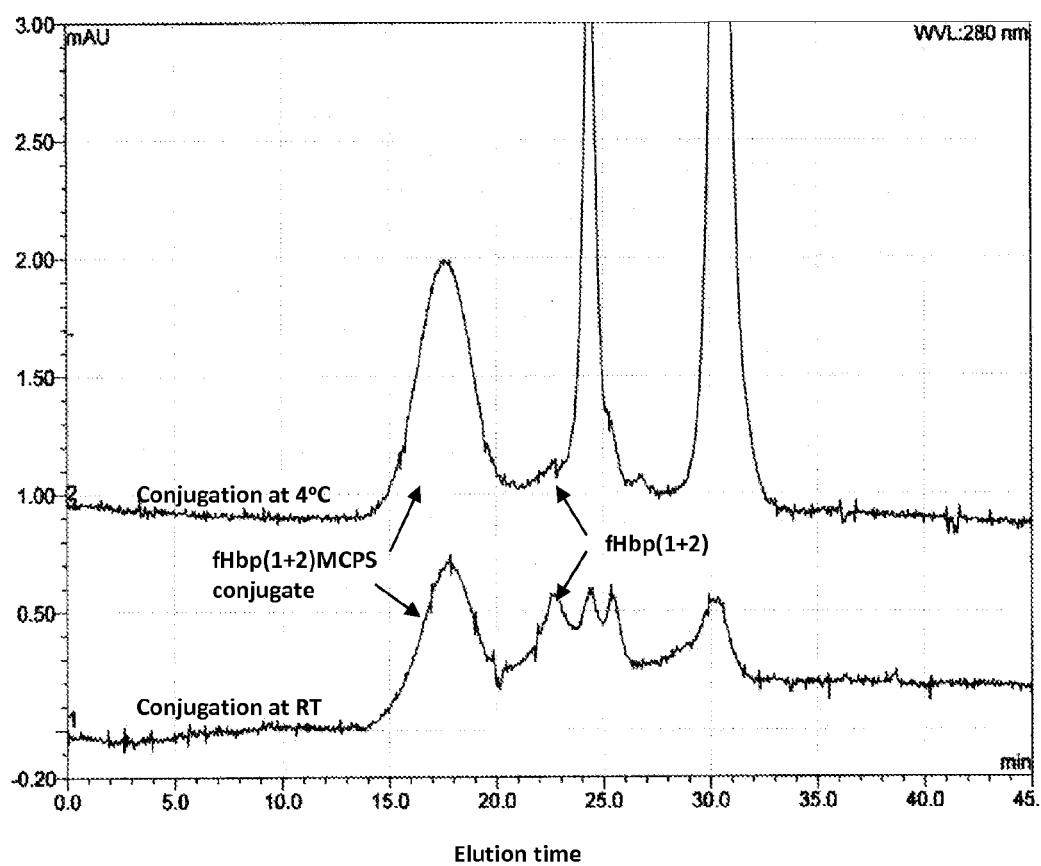
FIG. 2 is a plot of size-exclusion HPLC profiles (monitored at 280 nm) of conjugate products of fHbp(1+2) and meningococcal serogroup C polysaccharide (MCPS) prepared under the original conjugation conditions (bottom trace; room temperature) or the modified conjugation conditions (top trace; 4° C.). fHbp(1+2)MCPS conjugate indicates the PS-fHbp conjugate; fHbp(1+2) indicates the unconjugated fHbp protein.

The SDS-PAGE gels and Western blots of the purified fHbp1, fHbp2 and fHbp(1+2) proteins used for the production of the conjugate vaccine are shown in FIGS. 1A-B. The purified fHbp (1+2) protein was conjugated to PS either by the conventional CDAP conjugation method developed by Lees at al. (*Vaccine* 26:190-198, 1996) which required 2-2.5 minutes activation time of PS at room temperature in order to achieve maximal yield or by the modified method where activation of PS with CDAP was performed at 4° C. for 1.5 to 2 hours. Size exclusion HPLC profiles of the products of the two methods showed that the modified method resulted in higher conjugation yield when compared to the conventional method (FIG. 2).

Figure 3B:
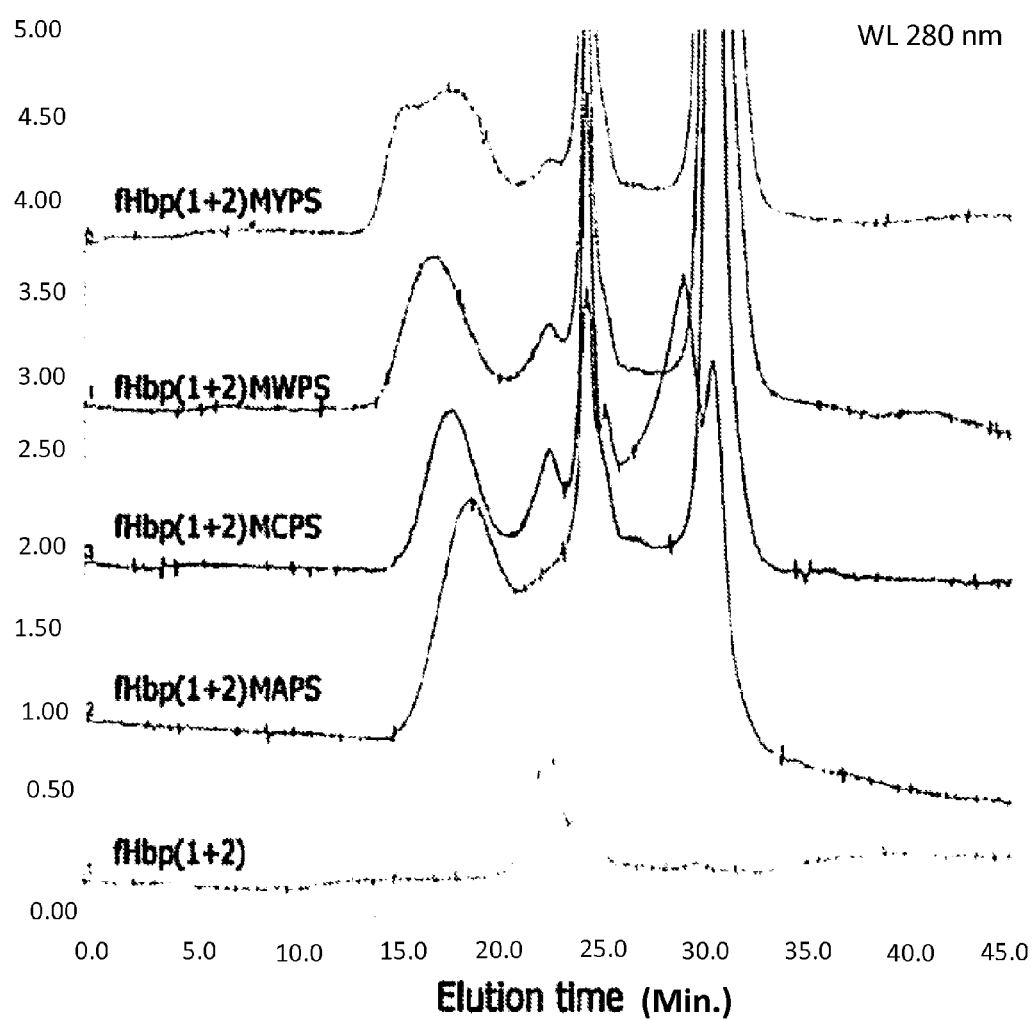

The modified conjugation method was used for the subsequent conjugation of all the purified fHbp proteins to meningococcal polysaccharides. The size-exclusion HPLC profiles of fHbp1 and MCPS-fHbp1, MCPS-fHbp2 and MCPS-fHbp(1+2) conjugates, monitored at 280 nm, are shown in FIG. 3A, and those of fHbp(1+2) and its conjugates to MAPS, MCPS, MWPS and MYPS are shown in FIG. 3B. The peak of each of the fHbp1, fHbp2 and fHbp(1+2) is at 22-23 minutes. Conjugate formation between PS and the proteins is indicated by the shift of protein signal from 22-23 minute to higher molecular weight position at 15-19 minutes upon conjugation, with remaining leftover unconjugated protein residue unmoved.

Example 2

Immunogenicity of fHbp Conjugates

Methods

Groups of 5 or 10 NIH-Swiss mice were immunized subcutaneously with 0.1 mL inoculum containing conjugates prepared in Example 1 or mixture of fHbp and native PS (control) on days 0 and 14, and 28 with sera collected on day 35.

IMMUNLON® 1B plates (Dynatech) were coated with 100 µL of coating solution containing PBS, pH 7.4, native Mn A, C, W135 or Y PS (5 µg/mL) admixed with methylated human serum albumin (5 µg/mL), or 1 µg/mL fHbp1 or fHbp2 for two hours, and washed three times with 150 µL of washing buffer (PBS, pH 7.4, 0.05% TWEEN® 20 and 0.02% $NaN_3$). Serum samples or reference serum (assigned with 3,200 units/mL anti-Mn A, C, W135 or Y PS antibody, or 32,000 units/mL for anti-fHbp1 or fHbp2) were diluted with dilution buffer (PBS, pH 7.4, 4% newborn calf serum, 0.02% $NaN_3$) in a series of two-fold dilutions starting from 1:200. One hundred µL of these diluted specimens were applied to each well of the ELISA plates. Plates were incubated overnight at room temperature, washed three times with 150 µL washing buffer, and then incubated with 100 µL goat anti-mouse IgG Fc conjugated with alkaline phosphatase (1/3000 dilution in dilution buffer) for two hours. The plates were washed three times with 150 µL washing buffer and incubated with 100 µL p-nitrophenyl phosphate (1 mg/mL in 1 M Tris, pH 9 plus 0.3 mM $MgCl_2$) to develop color. Fifty µL of 1 N NaOH was added to stop the reaction and the absorbance was measured with an ELISA plate reader (Model EL800, Bio-Tek, Winooski, Vt.) at 405 nm. The antibody levels of the samples were calculated from the readings based on the standard curve of the reference serum co-assayed in the same plate. The geometric mean of antibody level for each mouse group was calculated.

Results

Mice immunized with MCPS conjugates to fHbp1, fHbp2 and fHbp(1+2) mounted a strong IgG response to both the carrier proteins fHbp1, fHbp2 and fHbp(1+2) and also the meningococcal C polysaccharide (Table 1). As expected, an immune response to the meningococcal C polysaccharide was not observed when the mice were immunized with the unconjugated mixture of proteins (fHbp1, fHbp2 and fHbp (1+2)) and meningococcal C polysaccharide. This suggests that fHbp1, fHbp2 and fHbp(1+2) can serve as effective carrier proteins enhancing the immunogenicity of the conjugated MCPS. Furthermore, the proteins in fHbp1MCPS, fHbp2MCPS and fHbp(1+2)MCPS conjugates could induce comparable antibody levels (units/mL) as the unconjugated protein in the control groups. Since the fusion protein fHbp(1+2) was capable of inducing a strong immune response to both fHbp1 and fHbp2, it was used as the carrier protein for subsequent experiments.

TABLE 1

Geometric mean ELISA IgG [Ab] level (units/mL)[a] in antisera from mice (n = 5) one week after immunizations of 1 µg conjugate or 1 µg protein plus 1 µg MCPS mixture (control)

| Immunogen | Antigens | | |
|---|---|---|---|
| | MCPS | fHbp1 | fHbp2 |
| fHbp1 + MCPS control | 518 | 7558 | |
| fHbp1MCPS conjugate | 17,332 | 242,257 | |
| fHbp2 + MCPS control | 692 | | 46,061 |
| fHbp2MCPS conjugate | 11,648 | | 47,553 |
| fHbp(1 + 2)MCPS conjugate | 16,565 | 175,413 | 47,302 |

[a]Assigned IgG [Ab] levels (units/mL) for reference sera: [anti-MCPS] = 3200; [anti-fHbp1] = 32,000; [anti-fHbp2] = 32,000

The geometric mean ELISA IgG levels against MAPS, MCPS, MWPS, MYPS, fHbp1 and fHbp2 induced by the conjugates in singular monovalent or combined formulations are shown in Table 2. Each conjugate induced much higher anti-PS IgG antibody compared to the control group injected with mixture of fHbp(1+2) and meningococcal groups A, C, W135 and Y PS (13,803-106,193 units/mL vs. 21-774 units/mL). The level of antibody against the carrier protein induced in mice immunized with the conjugate was similar to the level of antibody induced in mice immunized with the unconjugated carrier fHbp (1+2) protein (23,195-98,252 units/mL vs. 64,468 units/mL for fHbp1 component; and 10,611-35,327 units/mL vs. 6,393 units/mL for fHbp2 component). For the combined formulation, in full or one quarter dosage, similar levels of antibody were induced against respective PS antigens and carrier protein components compared to each singular conjugate component. Together, these data demonstrate that fHbp(1+2) can serve as an effective carrier protein for conjugates of meningococcal groups A, C, W135 and Y PS in singular monovalent or combined formulations.

TABLE 2

Geometric mean ELISA [IgG] level (units/mL)[a] in antisera from mice (n = 10) one week after immunizations of 1 μg fHbp(1 + 2) plus mixture (ACWY PS) of 1 μg each of MAPS, MCPS, MWPS, and MYPS (Group a), 1 μg each conjugate (Groups b-e), combined formulation (Group f), or ¼ amount of the combined formulation (Group g).

| | | Antigens | | | | | |
|---|---|---|---|---|---|---|---|
| Group | Immunogen | MAPS | MCPS | MWPS | MYPS | fHbp1 | fHbp2 |
| a | fHbp(1 + 2) + ACWY PS | 387 | 774 | 21 | 79 | 64,468 | 6393 |
| b | fHbp(1 + 2)MAPS conj. | 166,193 | | | | 23,195 | 11,330 |
| c | fHbp(1 + 2)MCPS conj. | | 52,448 | | | 98,252 | 35,327 |
| d | fHbp(1 + 2)MWPS conj. | | | 13,803 | | 28,109 | 10,611 |
| e | fHbp(1 + 2)MYPS conj. | | | | 71,986 | 45,535 | 15,412 |
| f | (b + c + d + e) | 29,760 | 12,829 | 8831 | 32,219 | 28,823 | 10,229 |
| g | (b + c + d + e) × ¼ | 33,214 | 9870 | 9638 | 31,214 | 30,930 | 9075 |

[a]Assigned IgG [Ab] levels (units/mL) for reference sera: [anti-MAPS] = 3200; [anti-MCPS] = 3200; [anti-MWPS] = 32,000; [anti-MYPS] = 32,000]; [anti-fHbp1] = 32,000; [anti-fHbp2] = 32,000

Example 3

Bactericidal Activity of Induced Antisera

Methods

The serum bactericidal assay was performed as previously described (Moran et al., Infect. Immun. 62:5290-295, 1994) using normal human serum pre-screened for lack of bactericidal activity against the test strain as a source of complement. Individual mouse sera from each group of mice were pooled before being tested in the serum bactericidal assay. Depending on the amount of serum available and the expected titer, the pooled mouse sera were tested using a starting dilution of 1:2 to 1:8. When starting dilutions of 1:4 or 1:8 were used, results were extrapolated to lower dilutions using a typical killing curve. The reciprocal of the highest dilution of serum that killed >50% of the bacteria was taken as the end point titer of the serum. If the percent kill was between 35% and 50% at the lowest dilution tested, the serum was assigned the titer of the next lower dilution. If the percent kill was between 0% and 35% the serum was assigned a titer two dilutions lower. If there was less than 50% killing at a dilution of 1:2, the serum was assigned a titer of 1:1. The highest dilution tested was 1:512. All the pre-vaccination sera from the mice lacked bactericidal antibodies against any of the test strains and were assigned a titer of 1:1.

Results

The bactericidal activity of the induced IgG antibody against fHbp(1+2) was tested against N. meningitidis serogroup B fHbp1-expressing strains 44/76 and 8570, and fHbp2-expressing strains 7608 and 8047, and serogroup X strains 9557, 9558, and 9559 shown in Table 3. The pre-bleed control group showed little bactericidal activity, and its titer was assigned with 1. Bactericidal antibodies to fHbp1-expressing serogroup B and X N. meningitidis strains were observed in the sera of mice immunized with the unconjugated mixture of fHbp(1+2) and serogroups A, C, W-135, and Y PS. While antibodies to fHbp2 were observed in the induced antisera, they were not found to be bactericidal. Bactericidal antibodies to fHbp1-expressing serogroup B and X N. meningitidis strains were also observed in the sera of mice immunized with fHbp(1+2) and serogroups A, C, W-135, and Y PS conjugates. Bactericidal antibodies to fHbp2 was variable in the sera of mice immunized with the conjugate, and in general the bactericidal antibodies to fHbp1 immunized with fHbp(1+2)MWPS conjugate was comparatively lower than the levels present in sera of mice immunized with the other fHbp(1+2) PS conjugates. In the combined formulation, the full dosage group (group f) had about the same bactericidal titer (titer 4) as the control group for serogroup B fHbp1-expressing strains and a reduced titer (titer 2) for serogroup X strains, while the ¼ dosage group had reduced titer (titer 2) for both groups B and X strains.

TABLE 3

Bactericidal titers against groups B and X meningococci (MB and MX, respectively) of pooled antisera from mice (n = 10; groups a-g) one week after immunizations of 1 μg fHbp(1 + 2) plus mixture (ACWY PS) of 1 μg each of MAPS, MCPS, MWPS, and MYPS (group a), 1 μg each conjugate (groups b-e), combined formulation (group f), or ¼ amount of the combined formulation (group g)

| | | MB Strains | | | | MX Strains | | |
|---|---|---|---|---|---|---|---|---|
| | | fHbp1 | | fHbp2 | | | | |
| Group | Immunogen | 44/76 | 8570 | 7608 | 8047 | 9557 | 9558 | 9559 |
| | Pre-bleed pool | 1 | 1 | 1 | 1 | 1 | 1 | |
| a | fHbp(1 + 2) + ACWY PS | 2 | 4 | 1 | 1 | 4 | 4 | 4 |
| b | fHbp(1 + 2) MAPS conj. | 4 | 4 | 2 | 2 | 4 | 8 | 4 |

TABLE 3-continued

Bactericidal titers against groups B and X meningococci (MB and MX, respectively) of pooled antisera from mice (n = 10; groups a-g) one week after immunizations of 1 μg fHbp(1 + 2) plus mixture (ACWY PS) of 1 μg each of MAPS, MCPS, MWPS, and MYPS (group a), 1 μg each conjugate (groups b-e), combined formulation (group f), or ¼ amount of the combined formulation (group g)

| | | MB Strains | | | | MX Strains | | |
| | | fHbp1 | | fHbp2 | | | | |
| Group | Immunogen | 44/76 | 8570 | 7608 | 8047 | 9557 | 9558 | 9559 |
|---|---|---|---|---|---|---|---|---|
| c | fHbp(1 + 2) MCPS conj. | 4 | 4 | 1 | 1 | 4 | 4 | 4 |
| d | fHbp(1 + 2) MWPS conj. | 2 | 2 | 1 | 2 | 2 | 1 | 2 |
| e | fHbp(1 + 2) MYPS conj. | 2 | 4 | 2 | 1 | 4 | 4 | 4 |
| f | (b + c + d + e) | 4 | 4 | 1 | 1 | 2 | 1 | 2 |
| g | (b + c + d + e) × ¼ | 2 | 2 | 1 | 1 | 2 | 2 | 2 |

The bactericidal activity of the PS-specific IgG antibody was measured by bactericidal assay against PS-homologous strains (4 strains for serogroups A and C and 3 strains for W-135 and Y) (Table 4). The pre-bleed and the mixture of ACWY PS and fHbp(1+2) control groups showed no bactericidal activity (titer 1). All the tested antisera induced by monovalent conjugates or combined formulations were found to be bactericidal to the tested PS-homologous strains (Table 4). Since the capsular polysaccharides from serogroups A, C, W-135 and Y are known to be non-immunogenic in mice, these data suggest that fHbp can indeed be used as a carrier protein for a conjugate vaccine which in turn would induce PS-specific IgG antibody. Comparing the bactericidal titer of the antisera induced by monovalent conjugates with that induced by the combined formulation at full as well as ¼ reduced dosage, serogroups A, C and Y monovalent conjugates induced antisera with equal or higher titer than the combined formulations. On the contrary, serogroup W-135 monovalent conjugate induced antisera with equal or lower titer than the combined formulations.

TABLE 4

Bactericidal titers against PS-homologous A, C, W-135, and Y strains of pooled antisera from mice (n = 10; groups a-g) one week after immunizations of 1 μg fHbp(1 + 2) plus mixture (ACWY PS) of 1 μg each of MAPS, MCPS, MWPS, and MYPS (group a), 1 μg each conjugate (groups b-e), combined formulation (group f), or ¼ amount of the combined formulation (group g)

| | | MA Strains | | | |
| Group | Immunogens | 5878 | 7891 | 8822 | 8991 |
|---|---|---|---|---|---|
| b | fHbp(1 + 2)MAPS conj | 16 | 256 | 32 | 16 |
| f | (b + c + d + e) | 8 | 256 | 16 | 8 |
| g | (b + c + d + e) × ¼ | 8 | 256 | 8 | 8 |

TABLE 4-continued

Bactericidal titers against PS-homologous A, C, W-135, and Y strains of pooled antisera from mice (n = 10; groups a-g) one week after immunizations of 1 μg fHbp(1 + 2) plus mixture (ACWY PS) of 1 μg each of MAPS, MCPS, MWPS, and MYPS (group a), 1 μg each conjugate (groups b-e), combined formulation (group f), or ¼ amount of the combined formulation (group g)

| | | MC Strains | | | |
| | | 5416 | 5660 | 8241 | 8837 |
|---|---|---|---|---|---|
| c | fHbp(1 + 2)MCPS conj. | 16 | 8 | 32 | 16 |
| f | (b + c + d + e) | 2 | 2 | 8 | 4 |
| g | (b + c + d + e) × ¼ | 4 | 2 | 8 | 4 |
| | | MW Strains | | | |
| | | 6309 | 7510 | 8122 | |
| d | fHbp(1 + 2)MWPS conj. | 64 | 8 | 32 | |
| f | (b + c + d + e) | 128 | 8 | 128 | |
| g | (b + c + d + e) × ¼ | 64 | 16 | 128 | |
| | | MY Strains | | | |
| | | 4463 | 6972 | 8020 | |
| e | fHbp(1 + 2)MYPS conj. | 4 | 16 | 8 | |
| f | (b + c + d + e) | 4 | 8 | 4 | |
| g | (b + c + d + e) × ¼ | 4 | 8 | 8 | |

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A pharmaceutical composition comprising:
   an immunogenic conjugate comprising a Meningococcal group A polysaccharide conjugated to an fHbp fusion protein comprising the amino acid sequence SEQ. ID.NO:8;
   an immunogenic conjugate comprising a Meningococcal group C polysaccharide conjugated to an fHbp fusion protein comprising the amino acid sequence SEQ. ID.NO:8;
   an immunogenic conjugate comprising a Meningococcal group W polysaccharide conjugated to an fHbp fusion protein comprising the amino acid sequence SEQ. ID.NO:8; and
   an immunogenic conjugate comprising a Meningococcal group Y polysaccharide conjugated to an fHbp fusion protein comprising the amino acid sequence SEQ. ID.NO:8.

2. The pharmaceutical composition comprising one or more immunogenic conjugates of claim 1 and a pharmaceutically acceptable carrier.

3. The pharmaceutical composition of claim 2, further comprising an adjuvant.

4. A method of eliciting an immune response to *Neisseria meningitidis* in a subject, comprising administering an effective amount of the pharmaceutical composition of claim 1 to the subject, thereby eliciting an immune response to *Neisseria meningitidis* in the subject.

5. The method of eliciting an immune response to *Neisseria meningitidis* in a subject, comprising administering an effective amount of the pharmaceutical composition of claim 2 to the subject, thereby eliciting an immune response to *Neisseria meningitidis* in the subject.

6. The method of eliciting an immune response to *Neisseria meningitidis* in a subject, comprising administering an effective amount of the pharmaceutical composition of claim 3 to the subject, thereby eliciting an immune response to *Neisseria meningitidis* in the subject.

* * * * *

SEQUENCE LISTING

<160> NUMBER OF SEQ ID NOS: 16

<210> SEQ ID NO 1
<211> LENGTH: 525
<212> TYPE: DNA
<213> ORGANISM: Neisseria meningitidis

<400> SEQUENCE: 1

| | |
|---|---:|
| tcagaatttg acgcgcacac cggcggacag ttcgccggaa cggacgtttt tgacagtgtt | 60 |
| gactttgccg atgtagttgt agcggtagcc ggcatccaaa tcgacattcg gggtaacggc | 120 |
| atagcttacg cccgtcaata cgccgaggcc gatggaggtt tggctgaagc tgtcgctgcc | 180 |
| gcccaagtcg acgaggcgc ggttgaggct caagcgcgcg ccgagatacg gtttgacggg | 240 |
| cgattgggtg tcgaagtcgt aaatggcgga cgcgccgatg ctgtaaagtt tgaaatcggt | 300 |
| ggatggggct ttatagtttt tgtagcgcgt gtaatcgacg gcgaagcgga ggtcgttgat | 360 |
| gcggtagcct gcggagatgc gcgggctgaa gcctttggca gaacctaaag agcttgaggc | 420 |
| ttttgcgtgt gcggcatcgg cttggacgta aaagccggat gcgccttccg ccagtgcggc | 480 |
| ggccgggaga gcgagggcaa tcagtgtggc aagtgctttt ttcat | 525 |

<210> SEQ ID NO 2
<211> LENGTH: 174
<212> TYPE: PRT
<213> ORGANISM: Neisseria meningitidis

<400> SEQUENCE: 2

Met Lys Lys Ala Leu Ala Thr Leu Ile Ala Leu Ala Leu Pro Ala Ala
1               5                   10                  15

Ala Leu Ala Glu Gly Ala Ser Gly Phe Tyr Val Gln Ala Asp Ala Ala
                20                  25                  30

His Ala Lys Ala Ser Ser Ser Leu Gly Ser Ala Lys Gly Phe Ser Pro
            35                  40                  45

Arg Ile Ser Ala Gly Tyr Arg Ile Asn Asp Leu Arg Phe Ala Val Asp
        50                  55                  60

Tyr Thr Arg Tyr Lys Asn Tyr Lys Ala Pro Ser Thr Asp Phe Lys Leu
65                  70                  75                  80

Tyr Ser Ile Gly Ala Ser Ala Ile Tyr Asp Phe Asp Thr Gln Ser Pro
                85                  90                  95

Val Lys Pro Tyr Leu Gly Ala Arg Leu Ser Leu Asn Arg Ala Ser Val
            100                 105                 110

Asp Leu Gly Gly Ser Asp Ser Phe Ser Gln Thr Ser Ile Gly Leu Gly
        115                 120                 125

Val Leu Thr Gly Val Ser Tyr Ala Val Thr Pro Asn Val Asp Leu Asp
    130                 135                 140

Ala Gly Tyr Arg Tyr Asn Tyr Ile Gly Lys Val Asn Thr Val Lys Asn
145                 150                 155                 160

Val Arg Ser Gly Glu Leu Ser Ala Gly Val Arg Val Lys Phe
                165                 170

<210> SEQ ID NO 3
<211> LENGTH: 765
<212> TYPE: DNA
<213> ORGANISM: Neisseria meningitidis

<400> SEQUENCE: 3

| | |
|---|---:|
| agcagtggag ggggtggtgt cgccgccgac atcggtgcgg ggcttgccga tgcactaacc | 60 |
| gcaccgctcg accataaaga caaaggtttg cagtctttga cgctggatca gtccgtcagg | 120 |
| aaaaacgaga aactgaagct ggcggcacaa ggtgcgaaaa aaacttatgg aaacggtgac | 180 |
| agcctcaata cggcaaaatt gaagaacgac aaggtcagcc gtttcgactt tatccgccaa | 240 |
| atcgaagtgg acgggcagct cattaccttg gagagtggag agttccaagt atacaaacaa | 300 |
| agccattccg ccttaaccgc ctttcagacc gagcaaatac aagattcgga gcattccggg | 360 |

```
aagatggttg cgaaacgcca gttcagaatc ggcgacatag cgggcgaaca tacatctttt    420
gacaagcttc ccgaaggcgg cagggcgaca tatcgcggga cggcgttcgg ttcagacgat    480
gccggcggaa aactgaccta caccatagat ttcgccgcca agcagggaaa cggcaaaatc    540
gaacatttga atcgccaga actcaatgtc gacctggccg ccgccgatat caagccggat    600
ggaaaacgcc atgccgtcat cagcggttcc gtcctttaca accaagccga aaaggcagt    660 tactccctcg gtatctttgg cggaaaagcc caggaagttg ccggcagcgc ggaagtgaaa    720
accgtaaacg gcatacgcca tatcggcctt gccgccaagc aataa                    765
```

<210> SEQ ID NO 4
<211> LENGTH: 253
<212> TYPE: PRT
<213> ORGANISM: Neisseria meningitidis

<400> SEQUENCE: 4

```
Ser Ser Gly Gly Gly Val Ala Ala Asp Ile Gly Ala Gly Leu Ala
1               5                   10                  15

Asp Ala Leu Thr Ala Pro Asp His Lys Asp Lys Gly Leu Gln Ser Leu
            20                  25                  30

Thr Leu Asp Gln Ser Val Arg Lys Asn Glu Lys Leu Lys Leu Ala Ala
        35                  40                  45

Gln Gly Ala Glu Lys Thr Tyr Gly Asn Gly Asp Ser Leu Asn Thr Gly
    50                  55                  60

Lys Leu Lys Asn Asp Lys Val Ser Arg Phe Asp Phe Ile Arg Gln Ile
65                  70                  75                  80

Glu Val Asp Gly Gln Leu Ile Thr Leu Glu Ser Gly Glu Phe Gln Val
                85                  90                  95

Tyr Lys Gln Ser His Ser Ala Leu Thr Ala Phe Gln Thr Glu Gln Ile
            100                 105                 110

Gln Asp Ser Glu His Ser Gly Lys Met Val Ala Lys Arg Gln Phe Arg
        115                 120                 125

Ile Gly Asp Ile Ala Gly Glu His Thr Ser Phe Asp Lys Leu Pro Glu
    130                 135                 140

Gly Gly Arg Ala Thr Tyr Arg Gly Thr Ala Phe Gly Ser Asp Asp Ala
145                 150                 155                 160

Gly Gly Lys Leu Thr Tyr Thr Ile Asp Phe Ala Ala Lys Gln Gly Asn
                165                 170                 175

Gly Lys Ile Glu His Leu Lys Ser Pro Glu Leu Asn Val Asp Leu Ala
            180                 185                 190

Ala Ala Asp Ile Lys Pro Asp Gly Lys Arg His Ala Val Ile Ser Gly
        195                 200                 205

Ser Val Leu Tyr Asn Gln Ala Glu Lys Gly Ser Tyr Ser Leu Gly Ile
    210                 215                 220

Phe Gly Gly Lys Ala Gln Glu Val Ala Gly Ser Ala Glu Val Lys Thr
225                 230                 235                 240

Val Asn Gly Ile Arg His Ile Gly Leu Ala Ala Lys Gln
                245                 250
```

<210> SEQ ID NO 5
<211> LENGTH: 762
<212> TYPE: DNA
<213> ORGANISM: Neisseria meningitidis

<400> SEQUENCE: 5

```
agcagtggag gcggcggtgt cgccgccgac atcggcgcgg ggcttgccga tgcactaacc    60
```

```
gcaccgctcg accataaaga caaaagtttg cagtctttga cgctggatca gtccgtcagg    120
aaaaacgaga aactgaagct ggcggcacaa ggtgcggaaa aaacttatgg aaacggcgac    180
agcctcaata cgggcaaatt gaagaacgac aaggtcagcc gcttcgactt tatccgtcaa    240
atcgaagtgg acgggcagct cattaccttg gagagcggag agttccaaat atacaaacag    300
gaccactccg ccgtcgttgc cctacagatt gaaaaaatca caaccccga caaaatcgac    360 agcctgataa accaacgctc cttccttgtc agcggtttgg gcggagaaca taccgccttc    420
aaccaactgc ctgacggcaa agccgagtat cacggcaaag cattcagctc cgacgatgct    480
ggcgaaaaac tgacctatac catagatttc gccgccaaac agggacacgg caaaatcgaa    540
cacctgaaaa caccccgagca aaatgtcgag cttgccgccg ccgaactcaa agcagatgaa    600
aaatcacacg ccgtcatttt gggcgacacg cgctacggca gcgaagaaaa aggcacttac    660
cacctcgccc ttttcggcga ccgcgcccaa gaaatcgccg gctcggcaac cgtgaagata    720
ggggaaaagg ttcacgaaat cggcatcgcc ggcaaacagt ag                      762
```

<210> SEQ ID NO 6
<211> LENGTH: 252
<212> TYPE: PRT
<213> ORGANISM: Neisseria meningitidis

<400> SEQUENCE: 6

```
Ser Ser Gly Gly Gly Val Ala Ala Asp Ile Gly Ala Gly Leu Ala
1               5                   10                  15

Asp Ala Leu Thr Ala Pro Asp His Lys Asp Lys Ser Leu Gln Ser Leu
            20                  25                  30

Thr Leu Asp Gln Ser Val Arg Lys Asn Glu Lys Leu Lys Leu Ala Ala
        35                  40                  45

Gln Gly Ala Glu Lys Thr Tyr Gly Asn Gly Asp Ser Leu Asn Thr Gly
    50                  55                  60

Lys Leu Lys Asn Asp Lys Val Ser Arg Phe Asp Phe Ile Arg Gln Ile
65                  70                  75                  80

Glu Val Asp Gly Gln Leu Ile Thr Leu Glu Ser Gly Glu Phe Gln Ile
                85                  90                  95

Tyr Lys Gln Asp His Ser Ala Val Val Ala Leu Gln Ile Glu Lys Ile
            100                 105                 110

Asn Asn Pro Asp Lys Ile Asp Ser Leu Ile Asn Gln Arg Ser Phe Leu
        115                 120                 125

Val Ser Gly Leu Gly Gly Glu His Thr Ala Phe Asn Gln Leu Pro Asp
    130                 135                 140

Gly Lys Ala Glu Tyr His Gly Lys Ala Phe Ser Ser Asp Asp Ala Gly
145                 150                 155                 160

Gly Lys Leu Thr Tyr Thr Ile Asp Phe Ala Ala Lys Gln Gly His Gly
                165                 170                 175

Lys Ile Glu His Leu Lys Thr Pro Glu Gln Asn Val Glu Leu Ala Ala
            180                 185                 190

Ala Glu Leu Lys Ala Asp Glu Lys Ser His Ala Val Ile Leu Gly Asp
        195                 200                 205

Thr Arg Tyr Gly Ser Glu Glu Lys Gly Thr Tyr His Leu Ala Leu Phe
    210                 215                 220

Gly Asp Arg Ala Gln Glu Ile Ala Gly Ser Ala Thr Val Lys Ile Gly
225                 230                 235                 240

Glu Lys Val His Glu Ile Gly Ile Ala Gly Lys Gln
                245                 250
```

<210> SEQ ID NO 7
<211> LENGTH: 1563
<212> TYPE: DNA
<213> ORGANISM: Artificial Sequence
<220> FEATURE:
<223> OTHER INFORMATION: nucelic acid encoding fHbp1-fHbp2 fusion protein

<400> SEQUENCE: 7

```
agcagtggag ggggtggtgt cgccgccgac atcggtgcgg ggcttgccga tgcactaacc      60
gcaccgctcg accataaaga caaaggtttg cagtctttga cgctggatca gtccgtcagg     120
aaaaacgaga aactgaagct ggcggcacaa ggtgcggaaa aaacttatgg aaacggtgac     180
agcctcaata cgggcaaatt gaagaacgac aaggtcagcc gtttcgactt tatccgccaa     240
atcgaagtgg acgggcagct cattaccttg gagagtggag agttccaagt atacaaacaa     300
agccattccg cctaaccgc ctttcagacc gagcaaatac aagattcgga gcattccggg     360
aagatggttg cgaaacgcca gttcagaatc ggcgacatag cgggcgaaca tacatctttt     420
gacaagcttc ccgaaggcgg cagggcgaca tatcgcggga cggcgttcgg ttcagacgat     480
gccggcggaa aactgaccta caccatagat ttcgccgcca agcagggaaa cggcaaaatc     540
gaacatttga atcgccaga actcaatgtc gacctggccg ccgccgatat caagccggat     600
ggaaaacgcc atgccgtcat cagcggttcc gtcctttaca accaagccga aaaggcagt     660
tactcccttcg gtatctttgg cggaaaagcc caggaagttg ccggcagcgc ggaagtgaaa     720
accgtaaacg gcatacgcca tatcggcctt gccaagcaag gtggaggcgg ttcaggcgga     780
ggtggctctg gcgtggcgg ttctagagga ggcggcggtg tcgccgccga catcggcgcg     840
gggcttgccg atgcactaac cgcaccgctc gaccataaag acaaaagttt gcagtctttg     900
acgctggatc agtccgtcag gaaaaacgag aaactgaagc tggcggcaca aggtgcggaa     960
aaacttatg gaaacggcga cagcctcaat acgggcaaat tgaagaacga caaggtcagc    1020
cgcttcgact ttatccgtca aatcgaagtg gacgggcagc tcattacctt ggagagcgga    1080
gagttccaaa tatacaaaca ggaccactcc gccgtcgttg ccctacagat tgaaaaaatc    1140
aacaaccccg acaaaatcga cagcctgata accaacgct ccttccttgt cagcggtttg    1200
ggcggagaac ataccgcctt caaccaactg cctgacggca agccgagta tcacggcaaa    1260
gcattcagct ccgacgatgc tggcggaaaa ctgacctata ccatagattt cgccgccaaa    1320
cagggacacg gcaaaatcga acacctgaaa acacccgagc aaaatgtcga gcttgccgcc    1380
gccgaactca agcagatga aaaatcacac gccgtcattt tgggcgacac gcgctacggc    1440
agcgaagaaa aaggcactta ccacctcgcc cttttcggcg accgcgccca gaaaatcgcc    1500
ggctcggcaa ccgtgaagat agggaaaag gttcacgaaa tcggcatcgc cggcaaacag    1560
tag                                                                 1563
```

<210> SEQ ID NO 8
<211> LENGTH: 520
<212> TYPE: PRT
<213> ORGANISM: Artificial Sequence
<220> FEATURE:
<223> OTHER INFORMATION: fHbp1-fHbp2 fusion protein

<400> SEQUENCE: 8

```
Ser Ser Gly Gly Gly Gly Val Ala Ala Asp Ile Gly Ala Gly Leu Ala
1               5                   10                  15
```

```
Asp Ala Leu Thr Ala Pro Asp His Lys Asp Lys Gly Leu Gln Ser Leu
            20                  25                  30

Thr Leu Asp Gln Ser Val Arg Lys Asn Glu Lys Leu Lys Leu Ala Ala
        35                  40                  45

Gln Gly Ala Glu Lys Thr Tyr Gly Asn Gly Asp Ser Leu Asn Thr Gly
    50                  55                  60

Lys Leu Lys Asn Asp Lys Val Ser Arg Phe Asp Phe Ile Arg Gln Ile
65                  70                  75                  80

Glu Val Asp Gly Gln Leu Ile Thr Leu Glu Ser Gly Glu Phe Gln Val
                85                  90                  95

Tyr Lys Gln Ser His Ser Ala Leu Thr Ala Phe Gln Thr Glu Gln Ile
            100                 105                 110

Gln Asp Ser Glu His Ser Gly Lys Met Val Ala Lys Arg Gln Phe Arg
        115                 120                 125

Ile Gly Asp Ile Ala Gly Glu His Thr Ser Phe Asp Lys Leu Pro Glu
    130                 135                 140

Gly Gly Arg Ala Thr Tyr Arg Gly Thr Ala Phe Gly Ser Asp Asp Ala
145                 150                 155                 160

Gly Gly Lys Leu Thr Tyr Thr Ile Asp Phe Ala Ala Lys Gln Gly Asn
                165                 170                 175

Gly Lys Ile Glu His Leu Lys Ser Pro Glu Leu Asn Val Asp Leu Ala
            180                 185                 190

Ala Ala Asp Ile Lys Pro Asp Gly Lys Arg His Ala Val Ile Ser Gly
        195                 200                 205

Ser Val Leu Tyr Asn Gln Ala Glu Lys Gly Ser Tyr Ser Leu Gly Ile
    210                 215                 220

Phe Gly Gly Lys Ala Gln Glu Val Ala Gly Ser Ala Glu Val Lys Thr
225                 230                 235                 240

Val Asn Gly Ile Arg His Ile Gly Leu Ala Lys Gln Gly Gly Gly Gly
                245                 250                 255

Ser Gly Gly Gly Gly Ser Gly Gly Gly Ser Arg Ser Ser Gly Gly
            260                 265                 270

Gly Gly Val Ala Ala Asp Ile Gly Ala Gly Leu Ala Asp Ala Leu Thr
        275                 280                 285

Ala Pro Asp His Lys Asp Lys Ser Leu Gln Ser Leu Thr Leu Asp Gln
    290                 295                 300

Ser Val Arg Lys Asn Glu Lys Leu Lys Leu Ala Ala Gln Gly Ala Glu
305                 310                 315                 320

Lys Thr Tyr Gly Asn Gly Asp Ser Leu Asn Thr Gly Lys Leu Lys Asn
                325                 330                 335

Asp Lys Val Ser Arg Phe Asp Phe Ile Arg Gln Ile Glu Val Asp Gly
            340                 345                 350

Gln Leu Ile Thr Leu Glu Ser Gly Glu Phe Gln Ile Tyr Lys Gln Asp
        355                 360                 365

His Ser Ala Val Val Ala Leu Gln Ile Glu Lys Ile Asn Asn Pro Asp
    370                 375                 380

Lys Ile Asp Ser Leu Ile Asn Gln Arg Ser Phe Leu Val Ser Gly Leu
385                 390                 395                 400

Gly Gly Glu His Thr Ala Phe Asn Gln Leu Pro Asp Gly Lys Ala Glu
                405                 410                 415

Tyr His Gly Lys Ala Phe Ser Ser Asp Asp Ala Gly Gly Lys Leu Thr
            420                 425                 430
```

```
Tyr Thr Ile Asp Phe Ala Ala Lys Gln Gly His Gly Lys Ile Glu His
            435                 440                 445

Leu Lys Thr Pro Glu Gln Asn Val Glu Leu Ala Ala Ala Glu Leu Lys
        450                 455                 460

Ala Asp Glu Lys Ser His Ala Val Ile Leu Gly Asp Thr Arg Tyr Gly
465                 470                 475                 480

Ser Glu Glu Lys Gly Thr Tyr His Leu Ala Leu Phe Gly Asp Arg Ala
                485                 490                 495

Gln Glu Ile Ala Gly Ser Ala Thr Val Lys Ile Gly Lys Val His
            500                 505                 510

Glu Ile Gly Ile Ala Gly Lys Gln
        515                 520

<210> SEQ ID NO 9
<211> LENGTH: 39
<212> TYPE: DNA
<213> ORGANISM: Artificial Sequence
<220> FEATURE:
<223> OTHER INFORMATION: synthetic oligonucleotide primer

<400> SEQUENCE: 9
aagcttcctc gagtgagcag tggaggggt ggtgtcgcc                       39

<210> SEQ ID NO 10
<211> LENGTH: 38
<212> TYPE: DNA
<213> ORGANISM: Artificial Sequence
<220> FEATURE:
<223> OTHER INFORMATION: Synthetic oligonucleotide primer

<400> SEQUENCE: 10
ggcggggaat tcacttattg cttggcggca aggccgat                       38

<210> SEQ ID NO 11
<211> LENGTH: 39
<212> TYPE: DNA
<213> ORGANISM: Artificial Sequence
<220> FEATURE:
<223> OTHER INFORMATION: Synthetic oligonucleotide primer

<400> SEQUENCE: 11
aagcttcctc gagtgagcag tggaggcggc ggtgtcgcc                      39

<210> SEQ ID NO 12
<211> LENGTH: 38
<212> TYPE: DNA
<213> ORGANISM: Artificial Sequence
<220> FEATURE:
<223> OTHER INFORMATION: Synthetic oligonucleotide primer

<400> SEQUENCE: 12
ggcggggaat tcacttacta ctgtttgccg gcgatgcc                       38

<210> SEQ ID NO 13
<211> LENGTH: 63
<212> TYPE: DNA
<213> ORGANISM: Artificial Sequence
<220> FEATURE:
<223> OTHER INFORMATION: Synthetic oligonucleotide primer

<400> SEQUENCE: 13
cgatccgcca ccgccagagc cacctccgcc tgaaccgcct ccaccttgct tggcaaggcc    60
gat                                                                 63
```

```
<210> SEQ ID NO 14
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 14
gccgcctcct ctagaaccgc caccgccaga gccacc                                36

<210> SEQ ID NO 15
<211> LENGTH: 63
<212> TYPE: DNA
<213> ORGANISM: Artificial Sequence
<220> FEATURE:
<223> OTHER INFORMATION: Synthetic oligonucleotide primer

<400> SEQUENCE: 15
ggtggaggcg gttcaggcgg aggtggctct ggcggtggcg gatcgggagg cggcggtgtc      60
gcc                                                                    63

<210> SEQ ID NO 16
<211> LENGTH: 33
<212> TYPE: DNA
<213> ORGANISM: Artificial Sequence
<220> FEATURE:
<223> OTHER INFORMATION: Synthetic oligonucleotide primer

<400> SEQUENCE: 16
ggtggcggtt ctagaggagg cggcggtgtc gcc                                   33
```